United States Patent
Ault-Riche et al.

(10) Patent No.: US 9,285,372 B2
(45) Date of Patent: Mar. 15, 2016

(54) METHODS AND COMPOSITIONS FOR IDENTIFYING D-PEPTIDIC COMPOUNDS THAT SPECIFICALLY BIND TARGET PROTEINS

(75) Inventors: Dana Ault-Riche, San Francisco, CA (US); Stephen B. H. Kent, San Francisco, CA (US); Sachdev S. Sidhu, Toronto (CA); Maruti Uppalapati, Toronto (CA)

(73) Assignees: Reflexion Pharmaceuticals, Inc., San Francisco, CA (US); The Governing Council of the University of Toronto, Toronto (CA)

( * ) Notice: Subject to any disclaimer, the term of this patent is extended or adjusted under 35 U.S.C. 154(b) by 1073 days.

(21) Appl. No.: 13/294,078

(22) Filed: Nov. 10, 2011

(65) Prior Publication Data
US 2012/0178643 A1    Jul. 12, 2012

Related U.S. Application Data

(60) Provisional application No. 61/413,316, filed on Nov. 12, 2010.

(51) Int. Cl.
C40B 30/04    (2006.01)
G01N 33/68    (2006.01)
C07K 14/315   (2006.01)

(52) U.S. Cl.
CPC .......... *G01N 33/6845* (2013.01); *C07K 14/315* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,780,221 A | 7/1998 | Schumacher et al. |
| 6,040,133 A | 3/2000 | Kent et al. |
| 6,548,279 B1 | 4/2003 | Kent et al. |
| 7,118,856 B2 | 10/2006 | Kent et al. |
| 7,408,026 B1 | 8/2008 | Kent et al. |
| 2010/0093624 A1 | 4/2010 | Low et al. |

FOREIGN PATENT DOCUMENTS

WO    WO0074728 A1    12/2000
WO    WO2010014830 A2    2/2010

OTHER PUBLICATIONS van Groen et al. (2008) ChemMedChem vol. 3 pp. 1848 to 1852.*
van Groen et al. (2008) ChemMedChem vol. 3 pp. 1848 to 1852 supporting information.*
Nord et al. (1997) Nature Biotechnology vol. 15 pp. 772 to 777.*
Alexander et al., "A minimal sequence code for switching protein structure and function", PNAS, 2009, vol. 106(50), 21149-21154.

(Continued)

*Primary Examiner* — Christian Boesen
(74) *Attorney, Agent, or Firm* — Bret E. Field; Glenn J. Foulds; Bozicevic, Field & Francis LLP

(57) ABSTRACT

Methods and compositions for identifying D-peptidic compounds that specifically bind target proteins are provided. Aspects of the methods include screening libraries of 20 residue or more L-peptidic compounds for specific binding to 40 residue or more D-target proteins. Once a L-peptidic compound has been identified that specifically binds to the D-target protein, the D-enantiomer of that compound may be produced.

17 Claims, 11 Drawing Sheets

(56) References Cited

OTHER PUBLICATIONS

Baker et al., "Computer-based redesign of a protein folding pathway", Nature Structural Biology, Jul. 2001, vol. 8(7), 602-605.

Baker et al., "Crystal structures and increased stabilization of the protein G variants with switched folding pathways NuG1 and NuG2", Protein Science, 2002, vol. 11, 2924-2931.

Binz et al. "Engineering novel binding proteins from nonimmunoglobulin domains," Nature Biotechnology, 2005, vol. 23, 1257-1268.

Byeon et al., "A Protein Contortionist: Core Mutations of GB1 that Induce Dimerization and Domain Swapping", J. Mol. Biol., 2003, vol. 333, 141-152.

Cochran et al., "Phage-display as a tool for quantifying protein stability determinants", Eur. J. Biochem., 2004, vol. 271, 1623-1629.

DeGrado et al., "Thermodynamic Genetics of the Folding of the B1 Immunoglobulin-Binding Domain From Streptococcal Protein G", Proteins: Structure, Function, and Genetics, Jan. 1995, vol. 21(1), 11-21.

Dintzis et al.,"A Comparison of the Immunogenicity of a Pair of Enantiomeric Proteins" Proteins: Structure, Function, and Genetics, 1993, vol. 16, 306-308.

Funke et al., "Mirror image phage display—a method to generate D-peptide ligands for use in diagnostic or therapeutical applications", Mol. BioSyst., 2009, vol. 5, 783-786.

Ghosh et al., "A Minimalist Approach toward Protein Recognition by Epitope Transfer from Functionally Evolved β-Sheet Surfaces" J. Am. Chem. Soc., 2006, vol. 128(44), 14356-14363.

Ghosh et al., "Inhibition of β-Amyloid Fibrillization by Directed Evolution of a β-Sheet Presenting Miniature Protein", J. Am. Chem. Soc., 2006, vol. 128(45), 14456-14457.

Gronenborn et al., "A Novel, Highly Stable Fold of the Immunoglobulin Binding Domain of Streptococcal Protein G", Science, 1991, vol. 253, 657-61.

Gronenborn et al., "Core mutants of the immunoglobulin binding domain of streptococcal protein G: stability and structural integrity", FEBS Letters, 1996, vol. 398, 312-316.

Kim et al., "Measurement of the β-sheet-forming propensities of amino acids", Nature, 1994, vol. 367, 660-663.

Kim et al., "Identification of D-peptide ligands through mirror-image phage display", Science, 1996, vol. 271, 1854-1857.

Mayo et al., "Design, structure and stability of a hyperthermophilic protein variant", Nature Structural Biology, 1998, vol. 5(6), 470-475.

Mayo et al., "Probing the role of packing specificity in protein design", Proc. Natl. Acad. Sci. USA, 1997, vol. 94, 10172-10177.

Rajashekhar et al., "Anti-proliferative Properties of novel D-Peptide-VEGF-Antagonists: Plausible Role in Anti-angiogenic and Anti-tumor Formation", FASEB J., Apr. 2009, vol. 23 (Meeting Abstract Supplement) 634.5.

Regan et al., "A Thermodynamic Scale for the Beta-Sheet Forming Tendencies of the Amino Acids", Biochemistry, 1994, vol. 33, 5510-5517.

Regan et al., "Guidelines for Protein Design: The Energetics of Beta-Sheet Side Chain Interactions", Science, 1995, vol. 270, 980-982.

Regan et al., "Novel metal-binding proteins by design", Structural Biology, May 1995, vol. 2(5), 368-373.

Willbold et al., "Mirror-image phage display: aiming at the mirror", ChemBioChem, 2003, vol. 4, 811-815.

Wunderlich et al. "In Vitro Evolution of a Hyperstable Gβ1 Variant", J. Mol. Biol., 2006, vol. 363, 545-557.

Blanco et al., "Exploring the conformational properties of the sequence space between two proteins with different folds: an experimental study", J Mol Biol (1999), 285(2):741-753.

Fellouse et al., "High-throughput generation of synthetic antibodies from highly functional minimalist phage-displayed libraries", J Mol Biol (2007), 373(4):924-940.

Mandal et al., "Chemical synthesis and X-ray structure of a heterochiral {D-protein antagonist plus vascular endothelial growth factor} protein complex by racemic crystallography", Proc Natl Acad Sci USA (2012),109 (37):14779-14784.

Pasupuleti et al., Preservation of antimicrobial properties of complement peptide C3a, from invertebrates to humans, J Biol Chem (2007), 282(4):2520-2028.

Tonikian et al., "Identifying specificity profiles for peptide recognition modules from phage-displayed peptide libraries", Nat Protoc (2007), 2(6):1368-1386.

\* cited by examiner

Figure 1
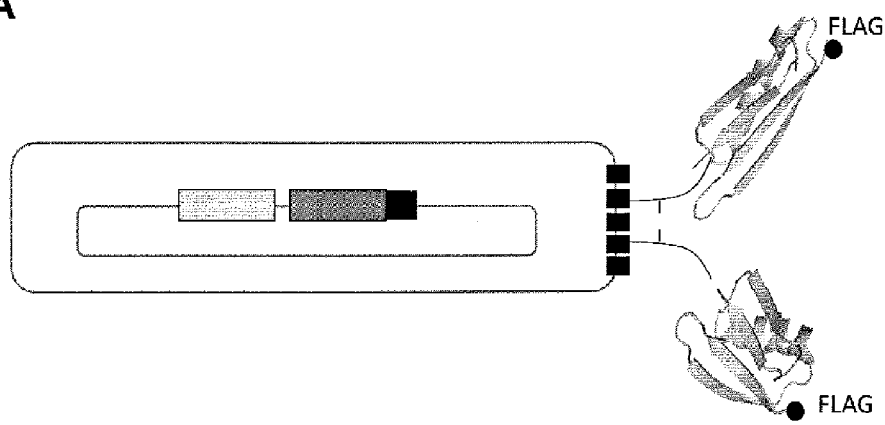
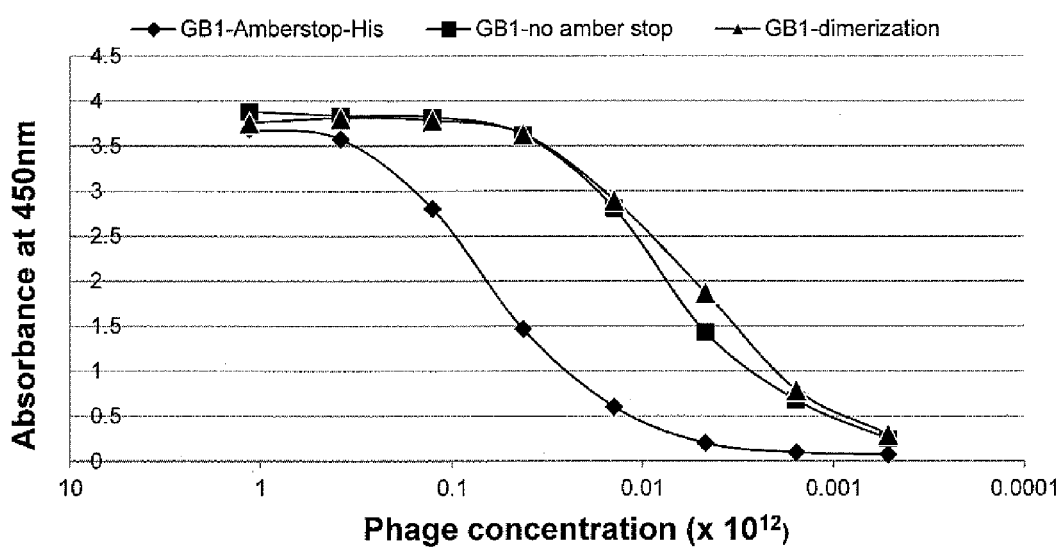

Figure 2

GB1 scaffold

| structure | | β1 ---> | | | | | | | | | ---- β2 ----> | | | | | | | | | | | ---------- α1 ---------> | | | | | | | | | | | | |
|---|---|---|---|---|---|---|---|---|---|---|---|---|---|---|---|---|---|---|---|---|---|---|---|---|---|---|---|---|---|---|---|---|---|---|---|
| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 |
| sequence | T | Y | K | L | I | L | N | G | K | T | L | K | G | E | T | T | T | E | A | V | D | A | A | T | A | E | K | V | F | K | Q | Y | A | N | D | N |

Library

| 1 | T | Y | K | L | I | L | N | G | K | T | L | K | G | E | T | T | T | E | A | V | D | A | A | T | A | E | K | V | F | K | Q | Y | A | N | D | N |
| 2 | T | Y | K | L | I | L | N | G | K | T | L | K | G | E | T | T | T | E | A | V | D | A | A | T | A | E | K | V | F | K | Q | Y | A | N | D | N |
| 3 | T | Y | K | L | I | L | N | G | K | T | L | K | G | E | T | T | T | E | A | V | D | A | A | T | A | E | K | V | F | K | Q | Y | A | N | D | N |
| 4 | T | Y | K | L | I | L | N | G | K | T | L | K | G | E | T | T | T | E | A | V | D | A | A | T | A | E | K | V | F | K | Q | Y | A | N | D | N |
| 5 | T | Y | K | L | I | L | N | G | K | T | L | K | G | E | T | T | T | E | A | V | D | A | A | T | A | E | K | V | F | K | Q | Y | A | N | D | N |
| 6 | T | Y | K | L | I | L | N | G | K | T | L | K | G | E | T | T | T | E | A | V | D | A | A | T | A | E | K | V | F | K | Q | Y | A | N | D | N |

SEQ ID NO: 1

GB1 scaffold

| structure | | | | | ---- β3 ----> | | | | | | | | ---- β4 ----> | | | | |
|---|---|---|---|---|---|---|---|---|---|---|---|---|---|---|---|---|---|---|
| position | 37 | 38 | 39 | 40 | 41 | 42 | 43 | 44 | 45 | 46 | 47 | 48 | 49 | 50 | 51 | 52 | 53 | 54 | 55 |
| sequence | G | V | D | G | E | W | T | Y | D | D | A | T | K | T | F | T | V | T | E |

Library

| 1 | G | V | D | G | E | W | T | Y | D | D | A | T | K | T | F | T | V | T | E | SEQ ID NO: 47 |
| 2 | G | V | D | G | E | W | T | Y | D | D | A | T | K | T | F | T | V | T | E | SEQ ID NO: 48 |
| 3 | G | V | D | G | E | W | T | Y | D | D | A | T | K | T | F | T | V | T | E | SEQ ID NO: 49 |
| 4 | G | V | D | G | E | W | T | Y | D | D | A | T | K | T | F | T | V | T | E | SEQ ID NO: 50 |
| 5 | G | V | D | G | E | W | T | Y | D | D | A | T | K | T | F | T | V | T | E | SEQ ID NO: 51 |
| 6 | G | V | D | G | E | W | T | Y | D | D | A | T | K | T | F | T | V | T | E | SEQ ID NO: 52 |

Figure 3

Library 1

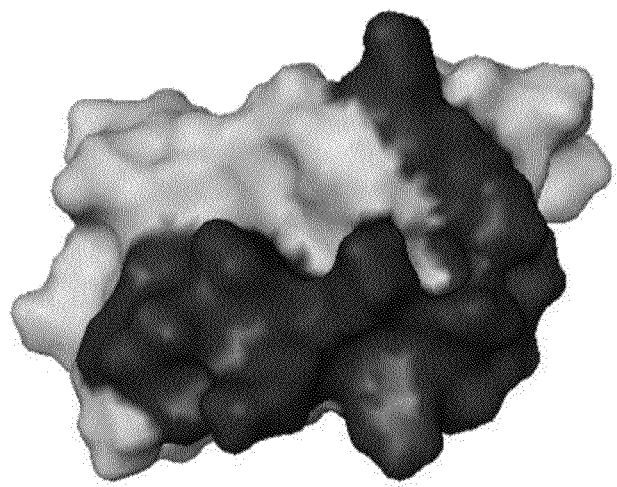

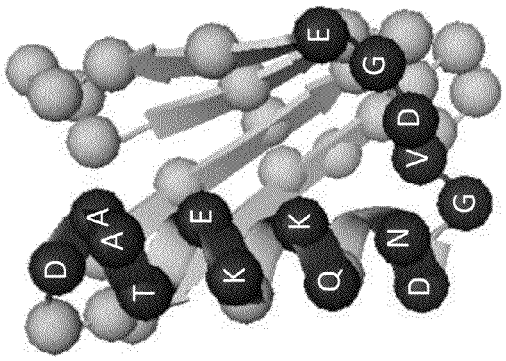

GATGATAAAGGCGGTAGCACGTACAAACTGATTCTGAACGGCAAAACCCTGAAACGACCGAAGCAGTGCAGCAAC
GGCAGAAAAAGTTTTCAAACAGTACGCCAACGATAATGGCCGTGGATGGACCTACGATGATGCGACGAAAACCTTCACGGTTAC
CGAAGGCGGTTCTGACAAAACT (SEQ ID NO:45)

D D K G G S T Y K L I L N G K T L K G E T T T E A V D A A T A E K V F K Q Y A N D N G V D G E W T Y D
D A T K T F T V T E G G S D K T (SEQ ID NO:46)

ACGACCGAAGCAGTGKHTKHTKHTGCAKHTKHTGTTTTCKHTKHTACGCCKHTKHTAATKHTKHTKHTGGACCTACG
ATGAT (SEQ ID NO:12)
ACGACCGAAGCAGTGKHTKHTKHTGCAKHTKHTGTTTTCKHTKHTACGCCKHTKHTAATKHTKHTKHTGGACCT
ACGATGAT (SEQ ID NO:13)
ACGACCGAAGCAGTGKHTKHTKHTGCAKHTKHTGTTTTCKHTKHTACGCCKHTKHTAATKHTKHTKHTGGA
CCTACGATGAT (SEQ ID NO:14)

Figure 4

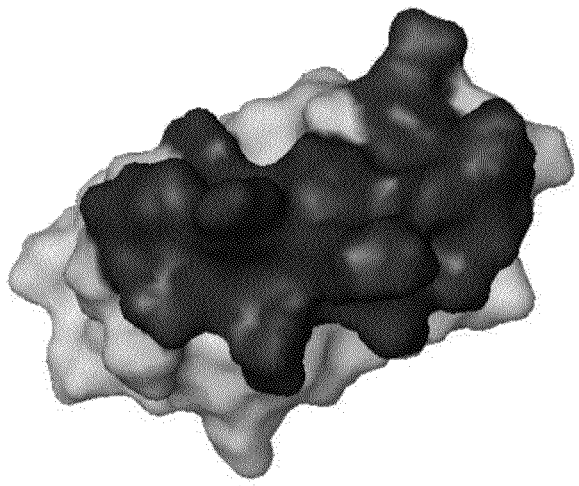

Library 2

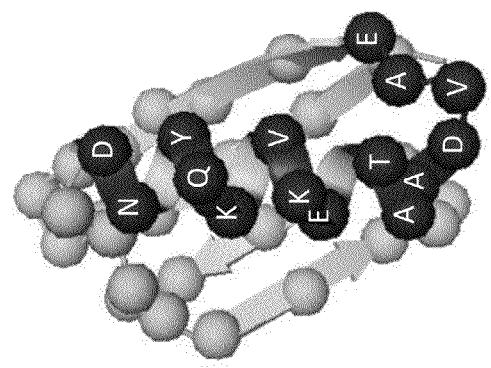

GATGATAAAGGGCGGTAGCACGTACAAACTGATTCTGAACGGCAAAACCCTGAAAGGTGAAACCACGACCGAAGCAGTGGATGCAGCAAC
GGCAGAAAAAGTTTTCAAACAGTACGCCAACGATAATGGCGTGGATGGAGAATGGACCTACGATGATGCGACGAAAACCTTCACGGTTA
CCGAAGGCGGTTCTGACAAAACT (SEQ ID NO:45)

D D K G G S T Y K L I L N G K T L K G E T T T E A V D A A T A E K V F K Q Y A N D N G V D G E W T Y D
D A T K T F T V T E G G S D K T (SEQ ID NO:46)

GGTGAAACCACGACCKHTKHTKHTKHTGCAKHTKHTKHTTTCKHTKHTKHTGCCKHTKHTAATGGCGTGGATGGT
(SEQ ID NO:15)
GGTGAAACCACGACCKHTKHTKHTKHTGCAKHTKHTKHTTTCKHTKHTKHTGCCKHTKHTAATGGCGTGGATGGT
(SEQ ID NO:16)
GGTGAAACCACGACCKHTKHTKHTKHTGCAKHTKHTKHTKHTGCAKHTKHTKHTGCCKHTKHTAATGGCGTGGATGGT
(SEQ ID NO:17)

Figure 5

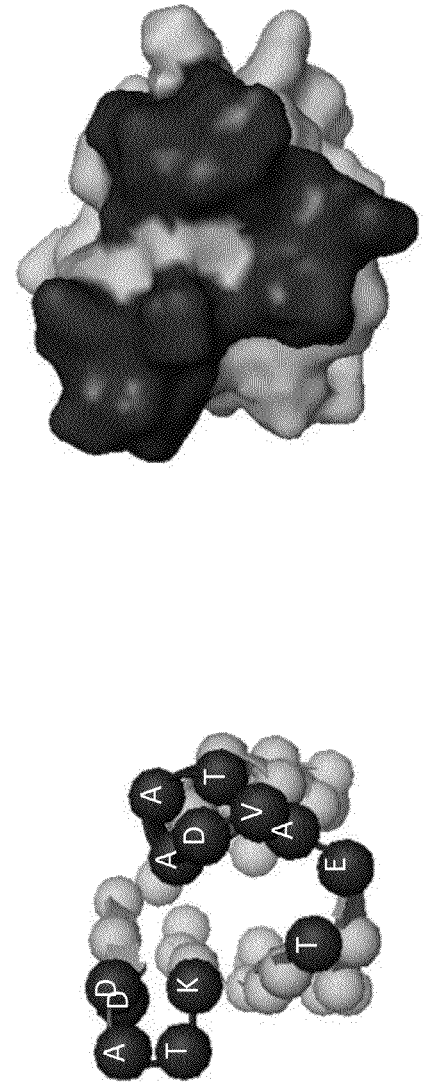

Library 3

GATGATAAAGGCGGTAGCACGTACAAACTGATTCTGAACGGCAAACCCTGAAAGGTGAAACCGACGAAGCAGTGGATGCAGCAA
CGGCAGAAAAAGTTTTCAAACAGTACGCCAACGATAATGGCGTGGATGGCGAATGGACCTACGATGATGCGACGAAAACCTTCACGGT
TACCGAAGGCGGTTCTGACAAAACT (SEQ ID NO:45)

D D K G G S I Y K L I L N G K T L K G E T T T E A V D A A T A E K V F K Q Y A N D N G V D G E W T Y
D D A T K T F T V T E G G S D K T (SEQ ID NO:46)

GATGATAAAGGCGGTAGC KHT KHT KHT KHT TACAAACTGATTCTGAAC (SEQ ID NO:18)

AAAGGTGAAACCACGACC KHT KHT KHT KHT KHT KHT KHT KHT KHT GCAGAAAAAGTTTTCAAA (SEQ ID NO:19)
AAAGGTGAAACCACGACC KHT KHT KHT KHT KHT KHT KHT KHT KHT GCAGAAAAAGTTTTCAAA (SEQ ID NO:20)
AAAGGTGAAACCACGACC KHT KHT KHT KHT KHT KHT KHT KHT KHT GCAGAAAAAGTTTTCAAA (SEQ ID NO:21)

GATGGTGAATGGACCTAC KHT KHT KHT KHT KHT KHT KHT KHT KHT ACCTTCACGGTTACCGAA (SEQ ID NO:22)
GATGGTGAATGGACCTAC KHT KHT KHT KHT KHT KHT KHT KHT KHT ACCTTCACGGTTACCGAA (SEQ ID NO:23)
GATGGTGAATGGACCTAC KHT KHT KHT KHT KHT KHT KHT KHT KHT ACCTTCACGGTTACCGAA (SEQ ID NO:24)

Figure 6

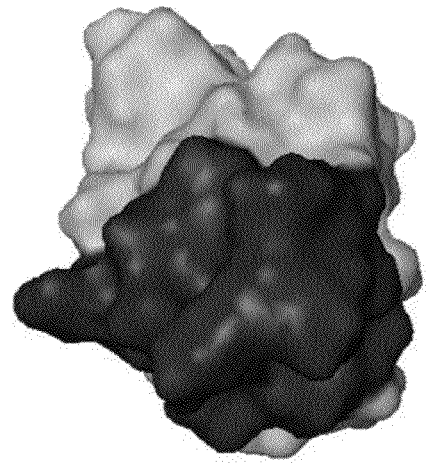

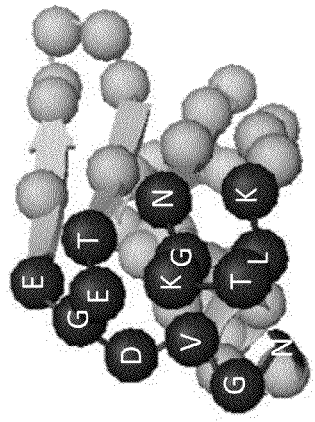

Library 4

GATGATAAAGGCGGTAGCACGTACAAACTGATTCTGAACGGCAAAACCCTGAAAGGTGAAACCACGACCGAAGCAGTGGATGCAGCA
ACGGCAGAAAAAGTTTTCAAACAGTACGCCAACGATAATGGGCGTGGATGGTGAATGGACCTACGATGATGCGACGAAAACCTTCACGG
TTACCGAAGGCGGTTCTGACAAAACT (SEQ ID NO:45)

D D K G G S T Y K L I L N G K T L K G E T T T E A V D A A T A E K V F K Q Y A N D N G V D G E W T Y
D D A T K T F T V T E G G S D K T (SEQ ID NO:46)

ACGTACAAACTGATTCTG KHT KHT KHT KHT KHT KHT KHT KHT GGTGAAACCACGACCGAA (SEQ ID NO:25)
ACGTACAAACTGATTCTG KHT KHT KHT KHT KHT KHT KHT KHT GGTGAAACCACGACCGAA (SEQ ID NO:26)
ACGTACAAACTGATTCTG KHT KHT KHT KHT KHT KHT KHT KHT GGTGAAACCACGACCGAA (SEQ ID NO:27)

AAACAGTACGCCAACGAT KHT KHT KHT KHT KHT KHT KHT KHT TGGACCTACGATGATGCG (SEQ ID NO:28)
AAACAGTACGCCAACGAT KHT KHT KHT KHT KHT KHT KHT KHT TGGACCTACGATGATGCG (SEQ ID NO:29)
AAACAGTACGCCAACGAT KHT KHT KHT KHT KHT KHT KHT KHT TGGACCTACGATGATGCG (SEQ ID NO:30)

ACGAAAACCTTCACGGTT KHT KHT KHT GGCGGTTCTGACAAAACT (SEQ ID NO:31)

Figure 7

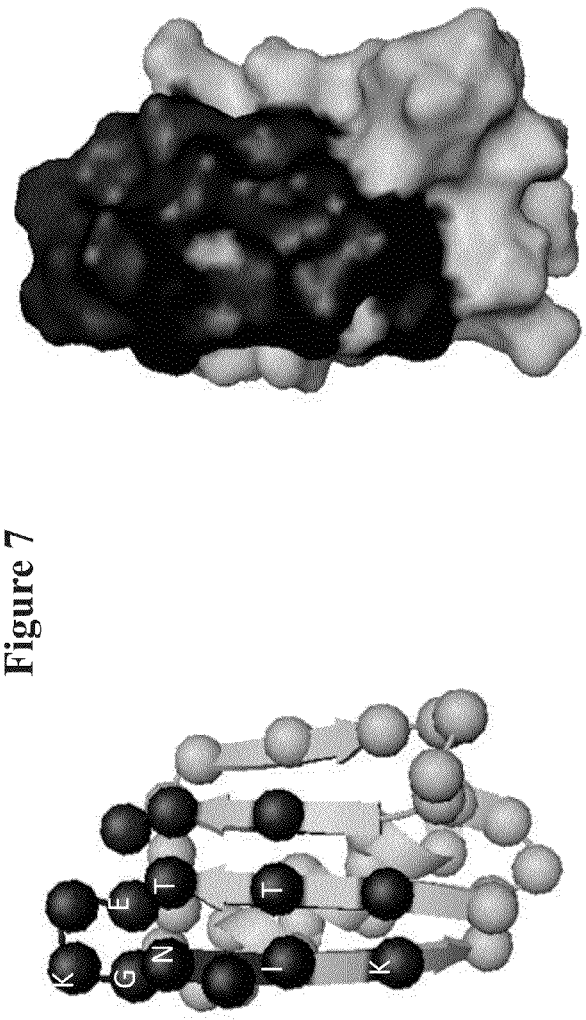

Library 5

GATGATAAAGGGCGGTAGCACGTACAAACTGATTCTGAACGGCAAAACCCTGAAAGGTGAAACCACGACCGAAGCAGTGGATGCAGCA
ACGGCAGAAAAAGTTTTCAAACAGTACGCCAACGATAATGGCGTGGATGGCGAATGGACCTACGATGATGCGACGAAAACCTTCACGG
TTACCGAAGGCGGTTCTGACAAAACT (SEQ ID NO:45)

D D K G G S T Y <u>K L I L N G K T L K G E T T T E</u> A V D A A T A E K V F K Q Y A N D N G V D G E W T Y
D D A T K T F <u>I V L E</u> G G S D K T (SEQ ID NO:46)

AAAGGCGGGTAGCACGTAC KHT CTG KHT CTG KHT CTG KHT CTG KHT CTG KHT CTG KHT CTG KHT ACC KHT ACCGAAGCAGTGGATGCA
(SEQ ID NO:32)
AAAGGCGGGTAGCACGTAC KHT CTG KHT CTG KHT CTG KHT CTG KHT CTG KHT CTG KHT ACC KHT ACCGAAGCAGTGGATGCA
(SEQ ID NO:33)
AAAGGCGGGTAGCACGTAC KHT CTG KHT CTG KHT CTG KHT CTG KHT CTG KHT CTG KHT ACC KHT ACCGAAGCAGTGGATGCA
(SEQ ID NO:34)
GATGCGACGAAAACCTTC KHT GTT KHT KHT KHT GGCGGTTCTGACAAAACT (SEQ ID NO:35)

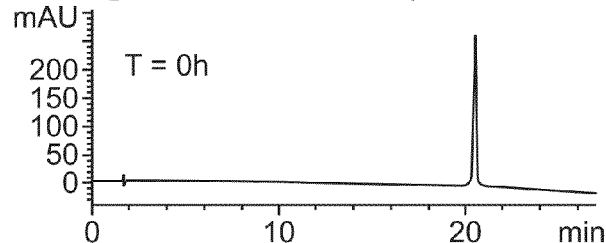
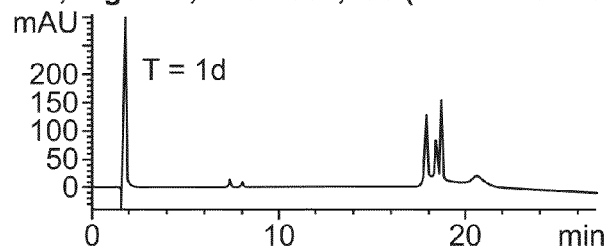
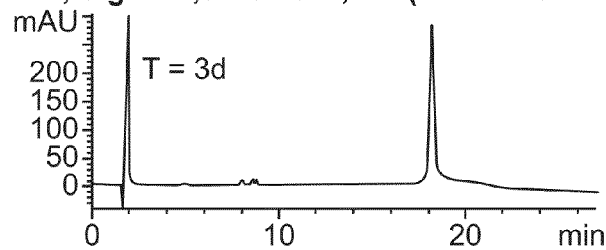
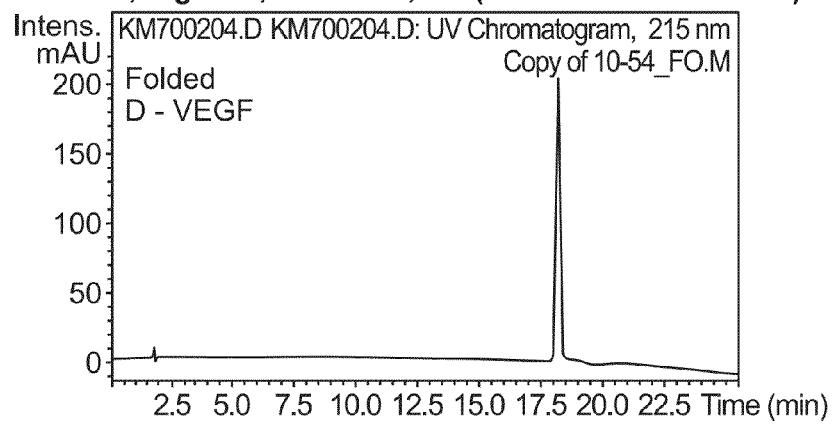
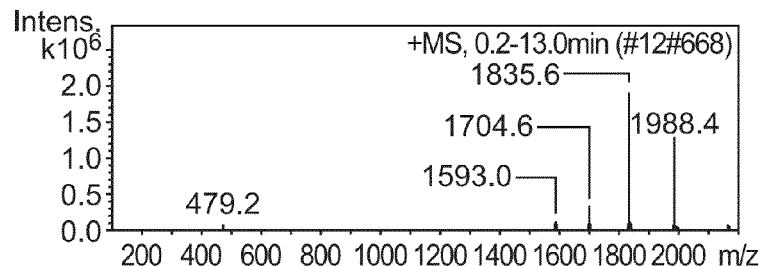
FIG. 10

METHODS AND COMPOSITIONS FOR IDENTIFYING D-PEPTIDIC COMPOUNDS THAT SPECIFICALLY BIND TARGET PROTEINS

CROSS REFERENCE TO RELATED APPLICATIONS

Pursuant to 35 U.S.C. §119(e), this application claims priority to the filing date of U.S. provisional application Ser. No. 61/413,316, filed Nov. 12, 2010, the disclosure of which is herein incorporated by reference.

This application is related to copending U.S. application entitled "GB1 peptidic libraries and methods of screening the same" filed on Nov. 10, 2011 to Sidhu et al. and accorded Ser. No. 13/294072, and U.S. provisional application Ser. No. 61/413,318 filed Nov. 12, 2010, which are entirely incorporated herein by reference.

This application is related to copending U.S. application entitled "GB1 peptidic compounds and methods for making and using the same" filed on Nov. 10, 2011 to Sidhu et al. and accorded Ser. No. 13/294097, and U.S. provisional application Ser. No. 61/413,331 filed Nov. 12, 2010, which are entirely incorporated herein by reference.

INTRODUCTION

Essentially all biological processes depend on molecular recognition mediated by proteins. The ability to manipulate the interactions of such proteins is of interest for both basic biological research and for the development of therapeutics.

Libraries of L-polypeptides can be prepared, e.g., by manipulating the immune system or via chemical synthesis, from which specificity of binding to target proteins can be selected. Molecular diversity from which specificity can be selected is large for polypeptides having numerous possible sequence combinations of amino acids. However, polypeptides composed of L-amino acids are prone to degradation by proteases and can elicit immunological responses when used in vivo, in contrast to the corresponding D-polypeptides.

Because of these properties of L-peptidic compounds, D-peptidic compounds that specifically bind to target proteins are of interest.

SUMMARY

Methods and compositions for identifying D-peptidic compounds that specifically bind target proteins are provided. Aspects of the methods include screening libraries of 20-mer or longer L-peptidic compounds for specific binding to 40-mer or longer D-target proteins. Once a L-peptidic compound has been identified that specifically binds to the D-target protein, the D-enantiomer of that compound may be produced.

BRIEF DESCRIPTION OF THE DRAWINGS

FIG. 1A depicts the phage display of a L-peptidic compound, e.g., a GB1 peptidic compound fusion of coat protein p3 that includes a hinge and dimerization format. FIG. 1B illustrates display levels of various formats of the L-peptidic compound fusion on the phage particles.

FIG. 2 illustrates exemplary L-peptidic libraries for use in the subject methods. The underlying sequence is of a GB1 scaffold domain (SEQ ID NO:1) where the positions of the variant amino acids in Libraries 1 to 6 are shown as dark blocks in the sequence (SEQ ID NO:1). The asterisks indicate positions (e.g., 1, 9, 19, 38, 47 and 55) at which mutations may include insertion of amino acids.

FIGS. 3 to 8 illustrate exemplary phage display libraries 1 to 6 of FIG. 2. Ribbon (left) and space filling (right) structural representations depict the variant amino acid positions in red. Oligonucleotide and amino acid sequences show the GB1 peptidic scaffold in the context of the fusion protein with GGS linkers at the N- and C-termini of the scaffold. Also shown are the oligonucleotide sequences synthesized for use in preparation of the libraries by Kunkel mutagenesis that include KHT codons at variant amino acid positions to encode variable regions of GB1 peptidic compounds.

FIG. 10 shows LC chromatograms that illustrate the folding of synthetic D-VEGF (top), and LC-MS data of purified folded D-VEGF (bottom).

DEFINITIONS

Figure 8:
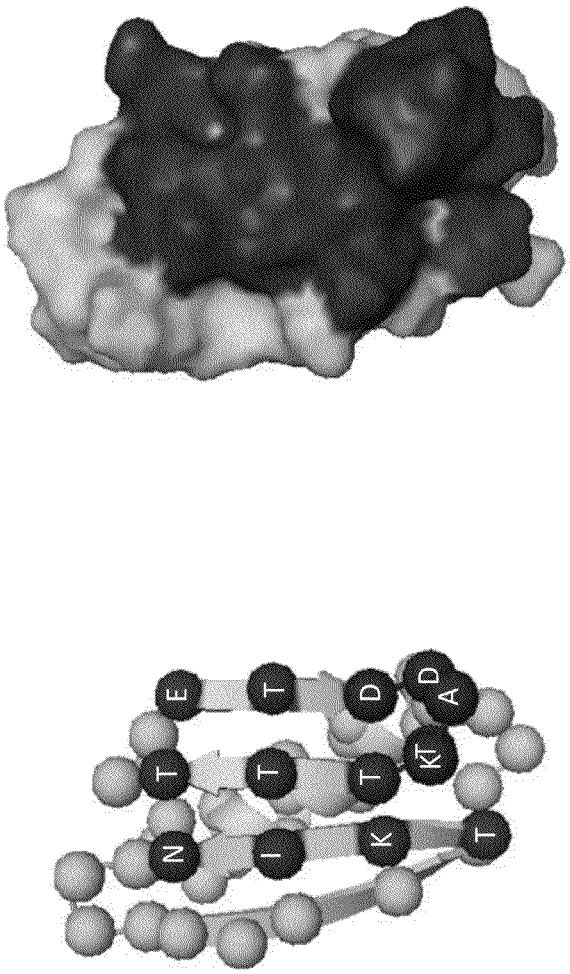

As used herein, the term "peptidic" refers to a moiety that is composed of amino acid residues. The term "peptidic" includes compounds or libraries in which the conventional backbone has been replaced with non-naturally occurring or synthetic backbones, and peptides in which one or more naturally occurring amino acids, or enantiomers thereof, have been replaced with one or more non-naturally occurring or synthetic amino acids, or enantiomers thereof. Any of the depictions of sequences found herein (e.g., using one-letter or three-letter codes) may represent a L-amino acid or a D-amino acid version of the sequence. Unless noted otherwise, the capital and small letter codes for L- and D-amino acid residues, respectively, are not utilized.

As used herein, the terms "polypeptide" and "protein" are used interchangeably. The term "polypeptide" also includes post translational modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids, or enantiomers thereof. In some instances, polypeptides may be of any length, e.g., 2 or more amino acids, 4 or more amino acids, 10 or more amino acids, 20 or more amino acids, 30 or more amino acids, 40 or more amino acids, 50 or more amino acids, 60 or more amino acids, 100 or more amino acids, 300 or more amino acids, 500 or more or 1000 or more amino acids.

As used herein, the terms "naturally occurring amino acid" and "non-naturally occurring amino acid" may be used to refer to both L- and D-versions of these amino acids. For example, a D-peptidic compound may be described as including naturally occurring amino acids, e.g., D-enantiomers of amino acids such as A, C, D, E, F, H, I, K, L, M, N, P, Q, R, S, T, V, W and Y.

As used herein, the term "scaffold" or "scaffold domain" refers to a peptidic framework from which a library of compounds arose, and against which the compounds are able to be compared. When a compound of a library arises from amino acid mutations at various positions within a scaffold, the amino acids at those positions are referred to as "variant amino acids." Such variant amino acids may confer on the resulting peptidic compounds different functions, such as specific binding to a target protein.

As used herein, the term "mutation" refers to a deletion, insertion, or substitution of an amino acid(s) residue or nucleotide(s) residue relative to a reference sequence, such as a scaffold sequence.

As used herein, the term "domain" refers to a continuous or discontinuous sequence of amino acid residues. As used herein, the term "region" refers to a continuous sequence of amino acid residues.

As used herein, the term "GB1 scaffold domain" refers to a scaffold that has a structure of the same structural motif as the B1 domain of Protein G (GB1), where the structural motif is characterized by a motif including a four stranded β-sheet packed against a helix (i.e., a 4β-1α motif). The arrangement of four β-strands and one α-helix may form a hairpin-helix-hairpin motif. An exemplary GB1 scaffold domain sequence is depicted in FIG. 2. GB1 scaffold domains include members of the family of IgG binding B domains, e,g, Protein L B1 domain. Amino acid sequences of exemplary B domains that may be employed herein as GB1 scaffold domains are found in the Wellcome Trust Sanger Institute Pfam database (The Pfam protein families database: Finn et al., Nucleic Acids Research (2010) Database Issue 38:D211-222), see, e.g., Family: IgG_binding_B (PF01378) (pfam.sanger.ac.uk/family/PF01378.10#tabview=tab0) or in NCBI's protein database. A GB1 scaffold domain may be a native sequence of a member of the B domain protein family, a B domain sequence with pre-existing amino acid sequence modifications (such as additions, deletions and/or substitutions), or a fragment or analogue thereof. A GB1 scaffold domain may be L-peptidic, D-peptidic or a combination thereof. In some cases, a "GB1 scaffold domain" may also be referred to as a "parent amino acid sequence."

In some embodiments, the GB1 scaffold domain is described by the following sequence: (T/S)Y(K/R)L(Z1)(Z1)(N/K)G(K/N/V/A)T(L/F)(K/S)GET(T/A/S)T(K/E)(A/T)(V/I)D(A/T/V)(A/E)(T/V)AE(K/Q)(A/E/T/V)F(K/R)(Q/D)YA(N/T)(A/D/E/K)N(G/N)(Z3)(D/T)G(E/V)W(A/T/S)YD(D/A/Y/T)ATKT(Z1)T(Z1)TE (SEQ ID NO:40), where each Z1 is independently a hydrophobic residue. In some embodiments, the GB1 scaffold domain is described by the following sequence: (T/S)Y(K/R)L(I/V)(L/I/V)(N/K)G(K/N/V/A)T(L/F)(K/S)GET(T/A/S)T(K/E)(A/T)(V/I)D(A/T/V)(A/E)(T/V)AE(K/Q)(A/E/T/V)F(K/R)(Q/D)YA(N/T)(A/D/E/K)N(G/N)(V/I)(D/T)G(E/V)W(A/T/S)YD(D/A/Y/T)ATKTFTVTE (SEQ ID NO:41). In certain embodiments, GB1 scaffold domain is described by the following sequence: TYKL(I/V)(L/I/V)(N/K)G(K/N)T(L/F)(K/S)GET(T/A)T(K/E)AVD(A/T/V)(A/E)TAE(K/Q)(A/E/T/V)F(K/R)QYA(N/T)(A/D/E/K)N(G/N)VDG(E/V)W(A/T/S)YD(D/A)ATKTFTVTE (SEQ ID NO:42). A mutation in a scaffold domain may include a deletion, insertion, or substitution of an amino acid residue at any convenient position to produce a sequence that is distinct from the reference scaffold domain sequence.

In some embodiments, the GB1 scaffold domain is described by the following sequence:

(SEQ ID NO: 43)
T(Z2)K(Z1)(Z1)(Z1)(N/V)(G/L/I)(K/G)(Q/T/D)(L/A/R)

(K/V)(G/E/V)(E/V)(A/T/R/I/P/V)(T/I)(R/W/L/K/V/T/I)

E(A/L/I)VDA(A/G)(T/E)(A/V/F)EK(V/I/Y)(F/L/W/I/A)K (L/Q)(Z1)(Z3)N(A/D)(K/N)(T/G)(V/I)(E/D)G(V/E)(W/F)

TY(D/K)D(E/A)(T/I)KT(Z1)T(Z1)TE, where each Z1 is independently a hydrophobic residue, Z2 is an aromatic hydrophobic residue, and Z3 is a non-aromatic hydrophobic residue.

In some embodiments, the GB1 scaffold domain is described by the following sequence:

(SEQ ID NO: 44)
T(Y/F/W/A)K(L/V/I/M/F/Y/A)(L/V/I/F/M)

(L/V/I/F/M/A/Y/S)(N/V)(G/L/I)(K/G)(Q/T/D)(L/A/R)

(K/V)(G/E/V)(E/V)(A/T/R/I/P/V)(T/I)

(R/W/L/K/V/T/I)E(A/L/I)VDA(A/G)(T/E)(A/V/F)EK (V/I/Y)(F/L/W/I/A)K(L/Q)(W/F/L/M/Y/I)(L/V/I/A)

N(A/D)(K/N)(T/G)(V/I)(E/D)G(V/E)(W/F)TY(D/K)

D(E/A)(T/I)KT(L/V/I/F/M/W)T(L/V/I/F/M)TE.

As used herein, the term "GB1 peptidic compound" refers to a compound composed of peptidic residues that has a parent GB1 scaffold domain.

As used herein, the term "parent amino acid sequence" is a polypeptide comprising an amino acid sequence from which a variant peptidic compound arose and against which the variant peptidic compound is being compared. In some cases, the parent polypeptide lacks one or more of the mutations or modifications disclosed herein and differs in function compared to a variant peptidic compound as disclosed herein. The parent polypeptide may include a native scaffold domain sequence (e.g., a GB1 scaffold domain) with pre-existing amino acid sequence modifications (such as additions, deletions and/or substitutions).

As used herein, the term "variable region" refers to a continuous sequence of residues that includes one or more variant amino acids. A variable region may also include one or more conserved amino acids at fixed positions. As used herein, the term "fixed region" refers to a continuous sequence of residues that does not include any mutations or variant amino acids, and is conserved across a library of compounds.

As used herein, the term "variable domain" refers to a domain that includes all of the variant amino acids or mutations of a peptidic scaffold. The variable domain may include one or more variable regions, and may encompass a continuous or a discontinuous sequence of residues.

As used herein, the term "discontinuous sequence of residues" refers to a sequence of residues that is not continuous with respect to the primary sequence of a peptidic compound. A peptidic compound may fold to form a secondary or tertiary structure, e.g., a 4β-1α motif, where the amino acids of a discontinuous sequence of residues are adjacent to each other in space, i.e., contiguous. As used herein, the term "continuous sequence of residues" refers to a sequence of residues that is continuous in terms of the primary sequence of a peptidic compound.

As used herein, the term "non-core mutation" refers to an amino acid mutation of a peptidic scaffold that is located at a position in the structure that is not part of the hydrophobic core of the structure, i.e., is not located at a hydrophobic core residue position. Amino acid residues at hydrophobic core positions are not significantly solvent exposed but rather tend to form intramolecular hydrophobic contacts. Unless explicitly defined otherwise, the hydrophobic core residue positions of a GB1 scaffold, as described herein, are defined by the positions 2, 4, 6, 19, 25, 29, 33, 38, 42, 51 and 53 of the scaffold. One criteria used to specify hydrophobic core residues in a scaffold is described by Dahiyat et al., ("Probing the role of packing specificity in protein design," Proc. Natl. Acad. Sci. USA, 1997, 94, 10172-10177) where a PDB structure of the GB1 scaffold was used to calculate which side chains expose less than 10% of their surface area to solvent. Such methods and criteria can be modified for use with any convenient scaffold.

As used herein, the term "surface mutation" refers to an amino acid mutation in a peptidic scaffold that is located at a position in the structure that is solvent exposed. Such variant amino acid residues at surface positions are capable of interacting directly with a target protein, whether or not such an interaction occurs. Solvent exposed residues may be determined using a Protein Data Bank (PDB) structure (e.g., 3 GB1 for a GB1 scaffold) and by estimating the solvent accessible surface area (SASA) for each residue using the GETarea tool (Fraczkiewicz & Braun, "Exact and efficient analytical calculation of the accessible surface areas and their gradients for macromolecules," J. Comput. Chem. 1998, 19, 319-333). This tool calculates the ratio of SASA in structure compared to SASA in a random coil, where the solvent accessible residues were differentiated from buried residues using a ratio of 0.4. For example, the solvent exposed residues of an exemplary GB1 scaffold determined using this method are shown in bold below: TYKLILNGKTLKGETTTEAVDAA-TAEKVFKQYANDNGVDGEWTYDDATKTFTVTE (SEQ ID NO:1). These methods may be readily modified to identify solvent exposed residues in any convenient scaffold domain described herein.

As used herein, the term "boundary mutation" refers to an amino acid mutation of a peptidic scaffold that is located at a position in the structure that is at the boundary between the hydrophobic core and the solvent exposed surface. Such variant amino acid residues at boundary positions may be in part contacting hydrophobic core residues and/or in part solvent exposed and capable of some interaction with a target protein, whether or not such an interaction occurs. Methods of classifying core, surface and boundary residues of a scaffold are described by Mayo et al. Nature Structural Biology, 5(6), 1998, 470-475 for the GB1 scaffold. Such methods may be modified for use with any convenient scaffold.

As used herein, the term "linking sequence" refers to a continuous sequence of amino acid residues, or analogs thereof, that connect two peptidic motifs. In certain embodiments, a linking sequence is the loop connecting two β-strands in a β-hairpin motif.

As used herein, the term "phage display" refers to a technique by which variant peptidic compounds are displayed as fusion proteins to a coat protein on the surface of phage, e.g. filamentous phage particles. The term "phagemid" refers to a plasmid vector having a bacterial origin of replication, e.g., ColE1, and a copy of an intergenic region of a bacteriophage. The phagemid may be based on any known bacteriophage, including filamentous bacteriophage. In some instances, the plasmid will also contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

As used herein, the term "phage vector" refers to a double stranded replicative form of a bacteriophage that contains a heterologous gene and is capable of replication. The phage vector has a phage origin of replication allowing phage replication and phage particle formation. In some cases. the phage is a filamentous bacteriophage, such as an M13, f1, fd, Pf3 phage or a derivative thereof, a lambdoid phage, such as lambda, 21, phi80, phi81, 82, 424, 434, etc., or a derivative thereof, a Baculovirus or a derivative thereof, a T4 phage or a derivative thereof, a T7 phage virus or a derivative thereof.

As used herein, the term "a target protein" refers to all members of the target family, and fragments and enantiomers thereof, and protein mimics thereof. The target proteins of interest that are described herein are intended to include all members of the target family, and fragments and enantiomers thereof, and protein mimics thereof, unless explicitly described otherwise. The target protein may be any protein of interest, such as a therapeutic or diagnostic target, including but not limited to: hormones, growth factors, receptors, enzymes, cytokines, osteoinductive factors, colony stimulating factors and immunoglobulins. It is understood that when the biological activities and functions of a target protein in vivo are being described herein, that what is being referred to are the activities of the L-target proteins. The term "target protein" is intended to include recombinant and synthetic molecules, which can be prepared using any convenient recombinant expression methods or using any convenient synthetic methods, or purchased commercially, as well as fusion proteins containing a target protein, as well as synthetic L- or D-proteins.

As used herein, the term "protein mimic" refers to a peptidic compound that mimics a binding property of a protein of interest, e.g., a target protein. In general terms, the target protein mimic includes an essential part of the original target protein (e.g., an epitope or essential residues thereof) that is necessary for forming a potential binding surface, such that the target protein mimic and the original target protein are each capable of binding specifically to a binding moiety of interest, e.g., an antibody or a D-peptidic compound. In some embodiments, the part(s) of the original target protein that is essential for binding is displayed on a scaffold such that potential binding surface of the original target protein is mimicked. Any suitable scaffold for displaying the minimal essential part of the target protein may be used, including but not limited to antibody scaffolds, scFv, anticalins, non-antibody scaffolds, mimetics of protein secondary and tertiary structures. In some embodiments, a target protein mimic includes residues or fragments of the original target protein that are incorporated into a protein scaffold, where the scaffold mimics a structural motif of the target protein. For example, by incorporating residues of the target protein at desirable positions of a convenient scaffold, the protein mimic may present a potential binding surface that mimics that of the original target protein. In some embodiments, the native structure of the fragments of the original target protein are retained using methods of conformational constraint. Any convenient methods of conformationally constraining a peptidic compound may be used, such as but not limited to, bioconjugation, dimerization (e.g., via a linker), multimerization, or cyclization.

As used herein, the terms "linker", "linking group" and "linkage" are used interchangeably and refer to a linking moiety that connects two groups and has a backbone of 30 atoms or less in length. A linking moiety may be a covalent bond that connects two groups or a chain of between 1 and 30 atoms in length, for example of about 1, 2, 3, 4, 5, 6, 8, 10, 12, 14, 16, 18, 20 or 30 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example an alkyl, aryl or alkenyl group. A linker may include, without limitations, oligo(ethylene glycol), ethers, thioethers, amides, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "affinity tag" refers to a member of a specific binding pair, i.e. two molecules where one of the molecules through chemical or physical means specifically binds to the other molecule. The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), and antigen and antibody, although binding pairs, e.g., nucleic acid hybrids, polyhistidine and nickel, and azido and alkynyl (e.g., cyclooctynyl) or phosphino groups are also envisioned. The specific binding pairs may include analogs, derivatives, fragments and mimics of the original specific binding members.

As used herein, the term "biotin moiety" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin moiety may also include a linker, e.g., -LC-biotin, -LC-LC-biotin, -SLC-biotin or -PEG$_n$-biotin where n is 3-12 (commercially available from Pierce Biotechnology).

The molecules of the subject methods may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids and polypeptides. The present invention is meant to include all such possible isomers, as well as, their racemic and optically pure forms. When the molecules described herein contain olefinic double bonds or other centers of geometric asymmetry, and unless specified otherwise, it is intended that the molecules include both E and Z geometric isomers. Likewise, all tautomeric forms are also intended to be included.

DETAILED DESCRIPTION

Methods and compositions for identifying D-peptidic compounds that specifically bind target proteins are provided. Aspects of the methods include screening libraries of 20-residue or more L-peptidic compounds for specific binding to 40-residue or more D-target proteins. Once a L-peptidic compound has been identified that specifically binds to the D-target protein, the D-enantiomer of that compound may be produced.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of producing D-peptidic compounds that specifically bind to L-target proteins of interest. D-peptidic compounds are enantiomers of L-peptidic compounds. D-peptidic compounds may be composed of D-amino acid residues. In some embodiments, the D-peptidic compounds are resistant to proteases and have long serum and/or saliva half-lives. In certain embodiments, the D-peptidic compounds have 10% or greater, such as 20% or greater, 30% or greater, 40% or greater, 50% or greater, 100% or greater, 200% or greater stability to a protease compared to a L-peptidic compound, in a protease stability assay such as that described by Tugyi et al. (2005), "Partial D-amino acid substitution: Improved enzymatic stability and preserved Ab recognition of a MUC2 epitope peptide", PNAS, 102, 413-418; and Fischer, P M. (2003). In certain embodiments, D-peptidic compounds can be systemically absorbed after oral administration. In certain embodiments, the D-peptidic compounds have low immunogenicity compared to an L-peptidic compound. In certain embodiments, the D-peptidic compounds are 10% or less, 20% or less, 30% or less, 40% or less, 50% or less, 70% or less, or 90% or less immunogenic compared to an L-peptidic compound, in an immunogenicity assay such as that described by Dintzis et al., "A Comparison of the Immunogenicity of a Pair of Enantiomeric Proteins" Proteins: Structure, Function, and Genetics 16:306-308 (1993).

One aspect of the subject methods of producing D-peptidic compounds includes screening L-peptidic libraries for binding to D-target proteins. By screening is meant contacting the target protein with a library of peptidic compounds and determining whether or not one or more members of the library specifically bind to the target. Aspects of the subject methods include contacting a sample containing a 40 residue or larger D-target protein with a 20 residue or larger L-peptidic library.

The D-target proteins may be D-enantiomers of any convenient target proteins, e.g., therapeutic or diagnostic targets, such that the D-enantiomers have a chiral specificity for ligands that is the opposite of the L-target protein. In some embodiments, the D-target protein is a D-peptidic fragment of a therapeutic or diagnostic target, e.g., a fragment that includes a particular motif of a the original target of interest. In some embodiments, the D-target protein is a D-peptidic mimic of a therapeutic or diagnostic target, or fragment thereof.

In some embodiments, the D-target protein comprises 30 or more amino acid residues, such as 35 or more, 40 or more, 45 or more, 50 or more, 55 or more, 60 or more, 65 or more, 70 or more, 75 or more, 80 or more, 85 or more, 90 or more, 95 or more, 100 or more, 110 or more, 120 or more, 125 or more, 130 or more, 140 or more, 150 or more, 175 or more, or 200 more residues. In certain embodiments, the 30 or more residues form a continuous sequence. In other embodiments, the 30 or more residues may be discontinuous, e.g., linked sequence fragments. In certain embodiments, the D-target protein includes a dimer of sequences, each sequence having 20 or more residues linked via a peptidic or non-peptidic linker. In certain embodiments, the D-target protein is 40 residues or larger, i.e., includes 40 or more residues, such as 65 or more residues. In some embodiments, the D-target protein has a MW of between 3,300 and 22,000 Da, such as between 4,400 and 22,000 Da, between 4,400 and 11,000 Da, between 4,400 and 8,800 Da, between 4,400 and 6,600 Da.

The D-target proteins are D-peptidic, e.g., composed of D-amino acids and glycine, and may be prepared using any convenient synthetic methods. In some embodiments, the D-target proteins are prepared using stepwise solid phase peptide synthesis methods, e.g., such as the stepwise addition of amino acids in a solid-phase Merrifield-type synthesis. Such methods may be used to prepare D-targets of high purity that are free from undesirable side products. For the synthesis of a D-target protein, D-amino acids or protected D-amino acids are utilized rather than the L-amino acids. D-amino acids suitable for polypeptide synthesis are commercially available, e.g., from the Peptide Institute (Osaka, Japan); Peptides International (Louisville, Ky.); Bachem Bioscience (Philadelphia, Pa.); and Bachem California, (Torrance, Calif.). A summary of some of the various methods available for synthesizing D-target proteins can be found in Steward et al., in "Solid Phase Peptide Synthesis", W.H. Freeman Co., San Francisco, 1969; Bodanszky et al., in "Peptide Synthesis", John Wiley & Sons, Second Edition, 1976 and Meienhofer, in "Hormonal Proteins and Peptides", Vol. 2, p. 46, Academic Press (New York), 1983; and Kent, Ann. Rev. Biochem., 57, 957, 1988, for solid phase peptide synthesis, and Schroder et al., in "The Peptides", Vol. 1, Academic Press (New York), 1965 for solution synthesis. Any convenient protecting group strategies may be used such as, but are not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based protecting groups may be used for the protection of sidechain functional groups. In Fmoc solid-phase peptide synthesis a Fmoc-amino protecting group is used at the amino terminal and tert-butyl or benzyl-based protecting groups may be used for protection of sidechain functional groups. Convenient protecting groups that may be used in such synthetic methods are described in the above references and by McOmic in "Protective Groups in Organic Chemistry", Plenum Press, New York, 1973; and Greene and Wuts, "Protective Groups in Organic Synthesis", John Wiley & Sons, 4th Edition, 2006.

In some embodiments, the D-target proteins are prepared by the assembly of polypeptide building blocks using native chemical ligation methods. In this procedure, two or more polypeptide fragments are first synthesized, that contain termini adapted for native chemical ligation or for kinetically controlled ligation. After stepwise chemical synthesis and cleavage from their respective solid phase resins, and after purification e.g. by reverse phase HPLC, two of the two or more polypeptides are mixed and reacted to join the adapted termini and form a larger, linear polypeptide that includes the two polypeptides linked by a native amide bond. Further native chemical ligation and/or kinetically controlled ligation reactions can then be performed to add further polypeptide fragments in a convergent synthetic strategy. For a review of native chemical ligation and kinetically controlled ligation methods for the preparation of proteins see, e.g., "Total chemical synthesis of proteins," Stephen B. H. Kent, Chem. Soc. Reviews, 38, 338-51 (2009). After the polypeptide chain corresponding to the D-target protein has been prepared, it is folded with concomitant formation of native disulfide bonds if such are present in the native L-protein target, to form the defined tertiary structure that is the mirror image of the native L-protein target.

Once the D-target protein has been produced, it may be optionally purified or used without further purification. Purification may be performed using any convenient method, for example, using chromatography (e.g., RP-HPLC, ion exchange, affinity, and sizing column chromatography), centrifugation, differential solubility, or any other convenient technique for the purification of proteins.

In some cases, the synthetic D-target protein that is produced exists in a random coil or an unfolded state. The D-target protein may then be folded using any convenient method, such that the D-target protein folds from the random coil or unfolded state into a characteristic three-dimensional structure. In some cases, folding a D-target protein includes dissolving the protein in an aqueous buffer under conditions that mimic physiological conditions (e.g., conditions of pH, ionic strength, temperature, and the like) and allowing the D-target protein to fold into a characteristic three-dimensional structure in solution over a period of time (e.g., 2 days). The progress of folding of the D-target protein may be followed using any convenient methods, such as HPLC, circular dichroism, etc. See, e.g., Boerema et al., ("Total synthesis by modern chemical ligation methods and high resolution (1.1 Å) X-ray structure of ribonuclease A," Peptide Science, 90(3), 278-286, 2008) for an exemplary folding method of a synthetic protein. The D-target protein may form a structure that is the mirror image of that of the L-target protein of interest. FIG. 10 illustrates the folding of an exemplary target protein, D-VEGF, in an aqueous solution over 2 days. In some cases, the protein folding solution is achiral. In some cases, the protein folding solution includes one or more chiral components, or enantiomers thereof, that may modulate the kinetics of protein folding.

The target proteins of interest may be any type of protein, such as a therapeutic or diagnostic target protein. Therapeutic target proteins may be any protein that is implicated in a disease, condition or disorder. The modulation of the biological activity of a therapeutic target protein may be used to prevent, treat and/or reduce the severity of a disease, condition or disorder. Diagnostic target proteins may be any proteins whose detection is desired for use in the diagnosis of a disease, condition or disorder. Therapeutic and diagnostic target proteins include, but are not limited to, disease-specific proteins. Disease-specific proteins are proteins that are expressed exclusively, or at a significantly higher level, in one or several diseased cells or tissues compared to other non-diseased cells or tissues in an animal. Therapeutic and diagnostic target proteins include, but are not limited to: hormones, growth factors, receptors, enzymes, cytokines, osteoinductive factors, colony stimulating factors, immunoglobulins, and fragments thereof.

In certain embodiments, the target protein may be one or more of the following: growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, Her-2, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins (e.g., an IL-4 or IL-8 protein), bone morphogenetic proteins, LIF, SCF, FLT-3 ligand, kit-ligand, SH3 domain, apoptosis protein, hepatocyte growth factor, hepatocyte growth factor receptor, neutravidin, and maltose binding protein.

In certain embodiments, the target protein may be a therapeutic target protein for which structural information is known, such as, but not limited to: Raf kinase (a target for the treatment of melanoma), Rho kinase (a target in the prevention of pathogenesis of cardiovascular disease), nuclear factor kappaB (NF-κB, a target for the treatment of multiple myeloma), vascular endothelial growth factor (VEGF) receptor kinase (a target for action of anti-angiogenetic drugs), Janus kinase 3 (JAK-3, a target for the treatment of rheumatoid arthritis), cyclin dependent kinase (CDK) 2 (CDK2, a target for prevention of stroke), FMS-like tyrosine kinase (FLT) 3 (FLT-3; a target for the treatment of acute myelogenous leukemia (AML)), epidermal growth factor receptor (EGFR) kinase (a target for the treatment of cancer), protein kinase A (PKA, a therapeutic target in the prevention of cardiovascular disease), p21-activated kinase (a target for the treatment of breast cancer), mitogen-activated protein kinase (MAPK, a target for the treatment of cancer and arthritis), c-Jun NH.sub.2-terminal kinase (JNK, a target for treatment of diabetes), AMP-activated kinase (AMPK, a target for prevention and treatment of insulin resistance), lck kinase (a target for immuno-suppression), phosphodiesterase PDE4 (a target in treatment of inflammatory diseases such as rheumatoid arthritis and asthma), Abl kinase (a target in treatment of chronic myeloid leukemia (CML)), phosphodiesterase PDE5 (a target in treatment of erectile dysfunction), a disintegrin and metalloproteinase 33 (ADAM33, a target for the treatment of asthma), human immunodeficiency virus (HIV)-1 protease and HIV integrase (targets for the treatment of HIV infection), respiratory syncytial virus (RSV) integrase (a target for the treatment of infection with RSV), X-linked inhibitor of apoptosis (XIAP, a target for the treatment of neurodegenerative disease and ischemic injury), thrombin (a therapeutic target in the treatment and prevention of thromboembolic disorders), tissue type plasminogen activator (a target in prevention of neuronal death after injury of central nervous system), matrix metalloproteinases (targets of anti-cancer agents preventing angiogenesis), beta secretase (a target for the treatment of Alzheimer's disease), src kinase (a target for the treatment of cancer), fyn kinase, lyn kinase, zeta-chain associated protein 70 (ZAP-70) protein tyrosine kinase, extracellular signal-regulated kinase 1 (ERK-1), p38 MAPK, CDK4, CDK5, glycogen synthase kinase 3 (GSK-3), KIT tyrosine kinase, FLT-1, FLT-4, kinase insert domain-containing receptor (KDR) kinase, and cancer osaka thyroid (COT) kinase.

In certain embodiments, the target protein is selected from the group consisting of a VEGF protein, a RANKL protein, a NGF protein, a TNF-alpha protein, a SH2 domain containing protein (e.g., a 3BP2 protein), a SH3 domain containing protein (e.g., an ABL protein, a Src protein, etc.), an IgE protein, a BLyS protein (Oren et al., "Structural basis of BLyS receptor recognition", Nature Structural Biology 9, 288-292, 2002), a PCSK9 protein (Ni et al., "A proprotein convertase subtilisin-like/kexin type 9 (PCSK9) C-terminal domain antibody antigen-binding fragment inhibits PCSK9 internalization and restores low density lipoprotein uptake", J. Biol. Chem. 2010 Apr. 23; 285(17):12882-91), a *Clostridium difficile* Toxin A or B (e.g., Ho et al., "Crystal structure of receptor-binding C-terminal repeats from *Clostridium difficile* toxin A", (2005) Proc. Natl. Acad. Sci. Usa 102: 18373-18378), and fragments thereof, and mimics thereof.

In some embodiments, the D-target protein is a D-peptidic fragment of a therapeutic or diagnostic target, e.g., a fragment that includes a particular motif of the original target of interest. In certain embodiments, the D-target protein is a D-peptidic fragment that corresponds to a domain of the original target protein of interest. In certain embodiments, the D-target protein is a D-peptidic fragment that corresponds to a structural motif of the original target protein of interest. In certain embodiments, the structural motif is a sequence of residues that folds to form a stable structure that mimics the structure of the original protein target. Such fragments may be of interest for ease of synthesis and/or for screening for specific binding to a particular motif of interest.

In some embodiments, the target protein is a target protein mimic of a therapeutic or diagnostic target, or fragment thereof. In certain embodiments, the target protein is a mimic of a native protein of interest, or a fragment thereof, that includes the minimum essential features of a potential binding surface of the target protein (e.g., an epitope). In certain embodiments, the target protein is a mimic that includes a sequence having 60% or greater amino acid sequence identity, such as 65% or greater, 70% or greater, 75% or greater, 80% or greater, 90% or greater, 95% or greater amino acid sequence identity to a fragment (e.g., an epitope) of an original protein of interest.

In some embodiments, the target protein is a D-target protein mimic, e.g., a compound that includes D-peptidic motifs that mimic an original target protein of interest, e.g., as described above.

In certain embodiments, the D-target protein includes one or more D-peptidic sequences corresponding to a binding motif of an original target protein of interest.

In certain embodiments, the D-target protein is a mimic that includes a sequence having 60% or greater amino acid sequence identity, such as 65% or greater, 70% or greater, 75% or greater, 80% or greater, 90% or greater, 95% or greater amino acid sequence identity to a fragment of an original target protein of interest. In certain embodiments, the D-target protein is a mimic that includes the minimum essential features of a binding motif displayed on a scaffold (e.g., a conformationally stabilized scaffold that closely mimics a motif of the original target protein).

In some embodiments, the production of a target protein mimic is of interest when the native target protein is large and/or not accessible by chemical synthesis, or when screening for binding to one particular motif of the original target protein is desired.

As summarized above, aspects of the screening methods include contacting a sample containing a 40 residue or more D-target protein with a 20 residue or more L-peptidic library.

In some embodiments, each compound of the L-peptidic library includes 30 or more residues, such as 40 or more, 50 or more, 60 or more, 70 or more, 80 or more, 90 or more, or 100 or more residues. In some embodiments, each compound of the L-peptidic library includes between 20 and 80 residues, such as between 30 and 80 residues, between 40 and 70 residues, between 45 and 60 residues, or between 52 and 58 residues. In certain embodiments, each compound of the subject library includes a peptidic sequence of 52, 53, 54, 55, 56, 57 or 58 residues. In certain embodiments, the peptidic sequence is of 55, 56 or 57 residues, such as 56 residues.

In some embodiments, each compound of the L-peptidic library includes a scaffold domain and a variable domain. The scaffold domain may have a structural motif that is conserved across the members of the library. The scaffold domain may fold to form a stable structure that includes a potential target protein binding surface that can carry variant amino acids without significantly disrupting the structure of the scaffold. The variant amino acids of the potential target binding surface may define a variable domain that is part of the scaffold domain. In some cases, the scaffold domain structure is not susceptible to unfolding in reducing intracellular environments, and does not significantly aggregate under physiological conditions.

A variety of scaffold domains may be used in the L-peptidic libraries. Scaffold domains of interest include but are not limited to non-immunoglobulin scaffold domains, such as those domains described in Table 1 of the review by Binz et al. ("Engineering novel binding proteins from nonimmunoglobulin domains," Nature Biotechnology 23, 1257-1268, 2005), which is entirely incorporated herein by reference.

In some embodiments, each compound of the L-peptidic library has a distinct variable domain that includes 5 or more, such as, 8 or more, 9 or more, 10 or more, 11 or more, 12 or more, 13 or more, 14 or more, or 15 or more mutations. The majority of mutations are included at various non-core positions of the scaffold, i.e., variant amino acids at non-core positions within a scaffold domain. The diversity of the libraries is designed to maximize diversity while minimizing structural perturbations of the scaffold domain. The positions to be mutated are selected to ensure that the compounds of the libraries can maintain a folded state under physiological conditions. Another aspect of generating diversity in the subject libraries is the selection of amino acid positions to be mutated such that the amino acids can form a potential binding surface in the scaffold domain, whether or not the residues actually bind a target protein. One way of determining whether an amino acid position is part of a potential binding surface involves examining the three dimensional structure of the scaffold domain, using a computer program such as the Chimera program (UCSF). Other ways include crystallographic and genetic mutational analysis. Any convenient method may be used to determine whether an amino acid position is part of a potential binding surface.

The mutations may be found at positions in the scaffold domain where the amino acid residue is at least in part solvent exposed. Solvent exposed positions can be determined using software suitable for protein modeling and three-dimensional structural information obtained from a crystal structure. The mutations of the scaffold domain may be concentrated at one of several different potential binding surfaces of the scaffold domain. In some instances, the majority of the mutations are at non-core positions of the scaffold domain (i.e., solvent exposed or boundary positions) however in some cases one or more mutations may be located at hydrophobic core positions. Mutations at such positions may confer desirable properties upon the resulting compound variant, such as stability, a certain structure, or specific binding to a target protein.

Another aspect of the diversity of the subject libraries is the size of the library, i.e, the number of distinct compounds of the library. In some embodiments, a subject library includes 50 or more distinct compounds, such as 100 or more, 300 or more, $1\times10^3$ or more, $1\times10^4$ or more, $1\times10^5$ or more, $1\times10^6$ or more, $1\times10^7$ or more, $1\times10^8$ or more, $1\times10^9$ or more, $1\times10^{10}$ or more, $1\times10^{11}$ or more, or $1\times10^{12}$ or more, distinct compounds.

In some embodiments, the scaffold domain is a GB1 scaffold domain, i.e., a scaffold domain of the same structural motif as the B1 domain of Protein G (GB1), where the structural motif of GB1 is characterized by a motif that includes an arrangement of four β-strands and one α-helix (i.e., a 4β-1α motif) around a hydrophobic core. In some embodiments, the four β-strands and one α-helix motifs of the structure are arranged in a hairpin-helix-hairpin motif, i.e., β1-β2-α1-β3-β4 where β1-β4 are β-strand motifs and α1 is a helix motif.

In certain embodiments, the L-peptidic library comprises 50 or more distinct compounds, where each of the 50 or more distinct compounds is a GB1 peptidic compound, and where each compound of the library comprises at least three different non-core mutations in a region outside of the β1-β2 region.

Exemplary GB1 peptidic libraries for use in the subject methods are described in the copending U.S. provisional application entitled "GB1 peptidic libraries and methods of screening the same" filed on the same day to Sidhu et al. and accorded Ser. No. 61/413,318, which is entirely incorporated herein by reference. FIG. 2 illustrates the sequences of exemplary GB1 peptidic libraries 1 to 6 and shows the positions of variant amino acids in the GB1 scaffold domain. FIGS. 3 to 8 illustrate phage display libraries 1 to 6 including the polynucleotide sequences that encode the variable regions of each library of L-peptidic compounds.

The L-peptidic libraries may be prepared by any convenient methods, such as, methods that find use in the preparation of libraries of peptidic compounds, for example, display methods (e.g., as described above). Any convenient display methods may be used to display the L-peptidic libraries, such as cell-based display techniques and cell-free display techniques. In certain embodiments, cell-based display techniques include phage display, bacterial display, yeast display and mammalian cell display. In certain embodiments, cell-free display techniques include mRNA display and ribosome display.

In some embodiments, the L-peptidic library is a phage display library. The phage display libraries may be rapidly and efficiently screened for those sequences that specifically bind to a D-target protein. In certain embodiments, the phage is a filamentous bacteriophage, such as an M13, f1, fd, Pf3 phage or a derivative thereof, or a lambdoid phage, such as lambda, 21, phi80, phi81, 82, 424, 434, M13KO7 helper phage, M13R408, M13-VCS, and Phi X 174, pJuFo phage system (J. Virol. 2001 August; 75(15):7107-13), hyperphage (Nat. Biotechnol. 2001 January; 19(1):75-8) etc., or a derivative thereof. In some embodiments, each compound of the L-peptidic library is fused to at least a portion of a viral coat protein. Examples of viral coat proteins include infectivity protein PIII, major coat protein PVIII, p3, Soc, Hoc, gpD (of bacteriophage lambda), minor bacteriophage coat protein 6 (pVI) (filamentous phage; J. Immunol. Methods, 1999, 231 (1-2):39-51), variants of the M13 bacteriophage major coat protein (P8) (Protein Sci 2000 April; 9(4):647-54). Any convenient methods for displaying fusion polypeptides including L-peptidic compounds on the surface of bacteriophage may be used. For example methods as described in patent publication numbers WO 92/01047; WO 92/20791; WO 93/06213; WO 93/11236 and WO 93/19172. In certain embodiments, the helper phage is M13KO7, and the coat protein is the M13 Phage gene III coat protein. In certain embodiments, the host is *E. coli* or protease deficient strains of *E. coli*. Vectors, such as the fth1 vector (Nucleic Acids Res. 2001 May 15; 29(10): E50-0) can be useful for the expression of the fusion protein.

Fusion polypeptides including L-peptidic compounds may be displayed on the surface of a cell or virus in a variety of formats and multivalent forms. See e.g., Wells and Lowman (1992) Curr. Opin. Struct. Biol B:355-362 and references cited therein. The multivalent forms of display have more than one target binding site which in some cases results in the identification of lower affinity clones and may also allow for more efficient sorting of rare clones during the selection process. In certain embodiments, a bivalent moiety such as an anti-MBP (maltose binding protein) Fab scaffold (a hinge and dimerization sequence from a Fab template), is used for displaying the L-peptidic compound variants on the surface of phage particles.

In monovalent phage display, a L-peptidic library may be fused to a coat protein (e.g., a gene III protein) or a portion thereof and expressed at low levels in the presence of wild type coat protein so that phage particles display one copy or none of the fusion proteins. Avidity effects are reduced relative to multivalent phage so that sorting is on the basis of intrinsic ligand affinity, and phagemid vectors are used, which simplify DNA manipulations. See e.g., Lowman and Wells (1991) Methods: A companion to Methods in Enzymology 3:205-216. In phage display, the phenotype of the phage particle, including the displayed polypeptide, corresponds to the genotype inside the phage particle, the DNA enclosed by the phage coat proteins.

The expression vector of a display system also can have a secretory signal sequence fused to the DNA encoding each L-peptidic compound. This sequence may be located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. In some cases, prokaryotic signal sequences may be obtained from genes encoding, for example, LamB or OmpF (Wong et al., Gene, 68:1931 (1983), MalE, PhoA and other genes. An exemplary prokaryotic signal sequence is the *E. coli* heat-stable enterotoxin II (STII) signal sequence as described by Chang et al., Gene 55:189 (1987), and malE.

The expression vector may also include a promoter to drive expression of the fusion protein. Promoters most commonly used in prokaryotic vectors include the lac Z promoter system, the alkaline phosphatase pho A promoter, the bacteriophage gamma-$_{PL}$ promoter (a temperature sensitive promoter), the tac promoter (a hybrid trp-lac promoter that is regulated by the lac repressor), the tryptophan promoter, and the bacteriophage T7 promoter. Any convenient microbial promoters may be used.

The expression vector may include other nucleic acid sequences, for example, sequences encoding gD tags, c-Myc epitopes, FLAG tags, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is fused to a L-peptidic compound which is not fused to the viral coat protein. Nucleic acid sequences encoding, for example, a polyhistidine tag, are useful for identifying fusion proteins including L-peptidic compounds that bind to a specific target using immunohistochemistry. Tags useful for detection of target binding can be fused to either a L-peptidic compound not fused to a viral coat protein or a L-peptidic compound fused to a viral coat protein.

In some cases, the expression vectors are phenotypic selection genes. The phenotypic selection genes are those encoding proteins that confer antibiotic resistance upon the host cell. By way of illustration, the ampicillin resistance gene (ampr), and the tetracycline resistance gene (tetr) are readily employed for this purpose.

The expression vector may also include nucleic acid sequences containing unique restriction sites and suppressible stop codons. The unique restriction sites are useful for moving L-peptidic compound domains between different vectors and expression systems. The suppressible stop codons are useful to control the level of expression of the fusion protein and to facilitate purification of L-peptidic compounds. For example, an amber stop codon can be read as Gln in a supE host to enable phage display, while in a non-supE host it is read as a stop codon to produce soluble L-peptidic compounds without fusion to phage coat proteins. These synthetic sequences can be fused to L-peptidic compounds in the vector.

In some cases, vector systems that allow the nucleic acid encoding a L-peptidic compound of interest to be easily removed from the vector system and placed into another vector system, may be used. For example, appropriate restriction sites can be engineered in a vector system to facilitate the removal of the nucleic acid sequence encoding the L-peptidic compounds. The restriction sequences are usually chosen to be unique in the vectors to facilitate efficient excision and ligation into new vectors. L-peptidic compound domains can then be expressed from vectors without extraneous fusion sequences, such as viral coat proteins or other sequence tags.

Between nucleic acid encoding L-peptidic compounds (gene 1) and the viral coat protein (gene 2), DNA encoding a termination codon may be inserted, such termination codons including UAG (amber), UAA (ocher) and UGA (opel). (Microbiology, Davis et al., Harper & Row, New York, 1980, pp. 237, 245-47 and 374). The termination codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., BioTechniques 5:376-379 (1987)). Any acceptable method may be used to place such a termination codon into the mRNA encoding the fusion polypeptide.

The suppressible codon may be inserted between the first gene encoding the L-peptidic compounds, and a second gene encoding at least a portion of a phage coat protein. Alternatively, the suppressible termination codon may be inserted adjacent to the fusion site by replacing the last amino acid triplet in the L-peptidic compound domain or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the L-peptidic compound domain is synthesized substantially without fusion to the phage coat protein due to termination at the inserted suppressible triplet UAG, UAA, or UGA. In the non-suppressor cell the L-peptidic compound domain is synthesized and secreted from the host cell due to the absence of the fused phage coat protein which otherwise anchored it to the host membrane.

As summarized above, aspects of the screening methods include contacting a sample containing a 40-mer or longer D-target protein with a 20-mer or longer L-peptidic library. The contacting step may be performed under conditions suitable for specifically binding members of the L-peptidic library with the D-target, whether or not such binding occurs. Such conditions include aqueous conditions in which D-target proteins of interest are able to be maintained in a folded state. In some cases, the conditions, including pH, ionic strength, temperature, and the like, mimic physiological conditions.

The contacting of the L-peptidic library and the D-target protein may be performed using any convenient method, such as, phage display screening methods, enzyme assay methods, ELISA assay methods, or other convenient biological assay methods for assessing specific binding or the inhibition of binding. The contacting step may be performed where the D-target is in solution phase or immobilized on a support, such as a beads, nanoparticles, planar surfaces or 96-well plates, gels, etc., that may include agarose, acrylamide, glass, silica, silicon, gold, plastic, cellulose, various acrylic copolymers, hydroxyalkyl methacrylates, polyacrylic and polymethacrylic copolymers, nylon, polystyrene, polyethylene or polypropylene, or the like. Attachment of the D-target protein to a support may be accomplished by any convenient methods, e.g., methods as described in Methods in Enzymology, 44 (1976), and Hermanson, "Bioconjugate Techniques" 2nd Edition, Academic Press, 2008. In some cases, the D-target protein can be attached to a detectable moiety, such as biotin. The contacting step may be performed where the L-peptidic library is in solution phase, or attached to a support such as a bead, a nanoparticle or an array, or displayed (e.g., on a phage particle).

Another aspect of the subject methods includes determining whether a compound of the L-peptidic libraries specifically bind to the D-target protein of interest. The determining step may be carried out using any one or more of a variety of protocols for characterizing the specific binding or the inhibition of binding. For example, the determining or assessment steps of ELISA assays, enzyme assays, or other related biological assay for assessing specific binding or the inhibition of binding. The determining step may include use of fluorescence, mass spectrometry, or other analytical methods used in immunoassays (e.g., colorimetric methods).

For example, the D-target may include a fluorescent label. Illustrative fluorescent labels include, for example, fluorescein isothiocyanate, didansyl chloride, lanthanides and lanthanide chelates, Alexafluor® dyes, inorganic semiconductor nanocrystals (e.g., quantum dots composed of or IIUV semiconductors), and similar labels. Any fluorescence emissions may be detected visually or may be detected using suitable instruments, such as fluorescence microscopes, fluorimeters, cameras, or instruments that include a charge coupled device, a photomultiplier tube, a diode array and the like. Other labels that emit light, e.g., phosphorescent labels, chemiluminescent labels, etc., may also be used and detected using similar techniques as those used in connection with fluorescence detection.

In some cases, a colorimetric label such as an enzyme, e.g., horseradish peroxidase, may be used. After an enzyme substrate, such as o-phenylenediamine dihydrochloride, is added to the enzyme a colored product is produced if the colorimetric label is present. The colored product may be detected visually or may be detected using suitable instruments such as, UV/visible instruments, plate readers, etc. In some examples, the colorimetric label may be a dye, e.g., an organic or an inorganic dye.

Other detectable markers that find use in the subject methods include a radiolabel. For example, the radiolabel may be integrated into the D-target or may be added as a tag to the species. Illustrative radiolabels include, but are not limited to, $^3$H, $^{14}$C, $^{32}$P, $^{33}$P, $^{35}$S and $^{125}$I.

Specific binding of L-peptidic compounds to D-target proteins may be measured using mass spectrometry. For example, the above species may be allowed a sufficient time to associate and the contents (after optional washing steps) of a particular complex, if formed, may be removed and analyzed using mass spectroscopy. Numerous different mass spectrometric techniques may be used. For example, matrix-assisted laser desorbed ionization (MALDI), electrospray ionization (ESI), fast atom bombardment (FAB), time of flight (TOF), MALDI/TOF, ESI/TOF, chemical ionization (CI), liquid secondary ion mass spectrometry (LSIMS) or other mass spectrometric techniques may be used. In some examples, tandem mass spectrometry may be performed. Mass spectrometric techniques are useful for distinguishing between association and non-association. In examples where mass spectrometry is used, an array may be generated on an appropriate substrate (e.g., a metal plate for MALDI). Identification of L-peptidic compounds that specifically bind D-target proteins may be accomplished, for example, by comparing the spectrometry data against databases of the L-peptidic library and the target proteins.

Any convenient proximity assays to assess specific binding may also be used. For example, the immobilized D-target may be labeled with a radioactive label. The L-peptidic compounds may include fluorescent labels, such that if specific binding of the two species occurs, radioactive emission will excite the fluorescent label, and fluorescence emission may be detected as a positive indicator of association. In some embodiments, the L-peptidic library is immobilized and the labeled D-target is in solution. Because this energy transfer process requires the radioactive label and the fluorescent label to be close, e.g., within a few microns, fluorescently labeled species that are not specifically bound would not emit light. Such proximity methods have the added benefit that no washing steps or separation steps are required to determine if association occurs.

The subject screening methods may also include in silico methods, in which one or more physical and/or chemical attributes of compounds of the L-peptidic libraries are expressed in a computer-readable format and evaluated by any one or more of a variety of molecular modeling and/or analysis programs and algorithms suitable for this purpose In some embodiments, the in silico method includes inputting one or more parameters related to the D-target protein, such as but not limited to, the three-dimensional coordinates of a known X-ray crystal structure of the D-target protein. In some embodiments, the in silico method includes inputting one or more parameters related to the compounds of the L-peptidic library, such as but not limited to, the three-dimensional coordinates of a known X-ray crystal structure of a parent scaffold domain of the library. In some instances, the in silico method includes generating one or more parameters for each compound in a peptidic library in a computer readable format, and evaluating the capabilities of the compounds to specifically bind to the target protein. The in silico methods include, but are not limited to, molecular modelling studies, biomolecular docking experiments, and virtual representations of molecular structures and/or processes, such as molecular interactions. The in silico methods may be performed as a pre-screen (e.g., prior to preparing a L-peptidic library and performing in vitro screening), or as a validation of binding compounds identified after in vitro screening.

Any convenient phage display screening methods may be used in the subject methods to screen the L-peptidic libraries. Screening for the ability of a fusion polypeptide including a compound of the L-peptidic library to bind a target protein can be performed in solution phase. For example, a D-target protein can be attached with a detectable moiety, such as biotin. Phage that bind to the D-target protein in solution can be separated from unbound phage by a molecule that binds to the detectable moiety, such as streptavidin-coated beads where biotin is the detectable moiety. Affinity of binders (L-peptidic compound fusions that bind to D-target protein) can be determined based on concentration of the D-target protein used, using any convenient formulas and criteria.

In some embodiments, the D-target protein may be attached to a suitable support. After attachment of the D-target protein to the support, the immobilized D-target is contacted with the phage library expressing the L-peptidic compound containing fusion polypeptides under conditions suitable for binding of at least a portion of the phage particles with the immobilized D-target. Bound particles ("binders") to the immobilized D-target protein are separated from those particles that do not bind to the D-target by washing. Wash conditions can be adjusted to result in removal of all but the higher affinity binders. Binders may be dissociated from the immobilized D-target by a variety of methods. These methods include, but are not limited to, competitive dissociation using a known ligand, altering pH and/or ionic strength. Selection of L-peptidic binders may involve elution from an affinity matrix with a ligand. Elution with increasing concentrations of ligand should elute displayed binding L-peptidic compounds of increasing affinity.

The L-peptidic binders can be isolated and then reamplified or expressed in a host cell and subjected to another round of selection for binding of D-target protein. Any number of rounds of selection or sorting can be utilized. One of the selection or sorting procedures can involve isolating binders that bind to an antibody to a polypeptide tag, such as antibodies to the gD protein, FLAG or polyhistidine tags. Another selection or sorting procedure can involve multiple rounds of sorting for stability, such as binding to a target protein that specifically binds to folded L-peptidic compound and does not bind to unfolded polypeptide followed by selecting or sorting the stable binders for binding to the D-target protein.

In some cases, suitable host cells are infected with the binders and helper phage, and the host cells are cultured under conditions suitable for amplification of the phagemid particles. The phagemid particles are then collected and the selection process is repeated one or more times until L-peptidic binders having the desired affinity for the D-target protein are selected. In certain embodiments, two or more rounds of selection are conducted.

After L-peptidic binders are identified by binding to the D-target protein, the nucleic acid can be extracted. Extracted DNA can then be used directly to transform $E.\ coli$ host cells or alternatively, the encoding sequences can be amplified, for example using PCR with suitable primers, and then inserted into a vector for expression.

One strategy to isolate high affinity binders is to bind a population of phage to an affinity matrix which contains a low amount of ligand. Phage displaying high affinity L-peptidic compound is bound and low affinity compounds are washed away. The high affinity L-peptidic compound is then recovered by elution with the ligand or by other procedures which elute the phage from the affinity matrix. In certain embodiments, the process of screening is carried out by automated systems to allow for high-throughput screening of library candidates.

In certain embodiments, the subject peptidic compounds specifically bind to a target protein with high affinity, e.g., as determined by an SPR binding assay or an ELISA assay. The subject peptidic compounds may exhibit an affinity for a target protein of 1 uM or less, such as 300 nM or less, 100 nM or less, 30 nM or less, 10 nM or less, 5 nM or less, 2 nM or less, 1 nM or less, 500 pM or less, or even less. The subject peptidic compounds may exhibit a specificity for a target protein, e.g., as determined by comparing the affinity of the compound for the target protein with that for a reference protein (e.g., an albumin protein), that is 5:1 or more 10:1 or more, such as 30:1 or more, 100:1 or more, 300:1 or more, 1000:1 or more, or even more.

As such, determining whether a L-peptidic compound of the library is capable of specifically binding a target protein may be carried out by any number of methods, as well as combinations thereof. Once a L-peptidic compound has been identified that specifically binds to the D-target protein, the D-enantiomer of that compound may be produced. The D-enantiomer can specifically bind to the L-enantiomer of the D-target protein.

The synthetic D-enantiomer of a polypeptide is capable of folding into a structure that is the mirror image of the corresponding L-polypeptide. This principle applies to both polypeptide ligands and to target proteins. Likewise, if a chiral ligand and target can specifically bind with each other to form a complex, then the enantiomers of the ligand and target also specifically bind to each other to form a mirror image complex with a structure that has mirror image symmetry to the original complex.

The D-peptidic compound may be prepared using any convenient method, e.g. solid phase peptide synthesis methods, solution phase peptide synthesis methods, native chemical ligation methods, or enzymatic ligation methods. In some embodiments, the D-peptidic compounds are prepared using stepwise solid phase peptide synthesis methods, e.g., such as the stepwise addition of amino acids in a solid-phase Merrifield-type synthesis. For the synthesis of a D-peptidic compound, D-amino acids or protected D-amino acids are utilized rather than the L-amino acids. Any convenient protecting group strategies that may be used such as, but not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based protecting groups may be used for protection of sidechain functional groups. In Fmoc solid-phase peptide synthesis, a Fmoc-amino protecting group is used at the amino terminal and tert-butyl or benzyl-based protecting groups may be used for protection of sidechain functional groups.

In some embodiments, the D-peptidic compounds are prepared by the assembly of polypeptide building blocks using native chemical ligation methods. In some cases, two polypeptide fragments are first synthesized that contain termini adapted for chemical ligation. After stepwise chemical synthesis and cleavage from their respective solid phase resins, the two polypeptides are mixed and reacted to join the adapted termini and produce a larger, linear polypeptide that includes the two polypeptides.

Once the D-peptidic compound has been produced, it may be optionally purified or used without further purification. Purification may be performed using any convenient method, for example, using chromatography (e.g., RP-HPLC, ion exchange, affinity, and sizing column chromatography), centrifugation, differential solubility, or any other convenient technique for the purification of proteins.

In some cases, after synthesis or purification, the D-peptidic compound exists in a random coil or an unfolded state. The D-peptidic compound may then be folded using any convenient method, such that the D-peptidic compound folds from the random coil or unfolded state into a characteristic three-dimensional structure. In some cases, folding the D-peptidic compound includes dissolving the compound in an aqueous buffer under conditions that mimic physiological conditions (e.g., conditions of pH, ionic strength, temperature, and the like) and allowing the compound to fold into a characteristic three-dimensional structure in solution over a period of time (e.g., 2 days). The progress of folding of the D-peptidic compound may be followed using any convenient methods, such as HPLC, circular dichroism, etc. See, e.g., Boerema et al., ("Total synthesis by modern chemical ligation methods and high resolution (1.1 Å) X-ray structure of ribonuclease A," Peptide Science, 90(3), 278-286, 2008) for an exemplary folding method of a synthetic protein. The D-peptidic compound may form a structure that is the mirror image of that of a corresponding L-enantiomer.

In some cases, the subject method further includes screening the synthesized D-peptidic compound for specific binding to the L-enantiomer of the D-target protein. This L-target protein may be a naturally occurring, a recombinant or fusion protein containing a target protein, or a synthetic protein, which can be prepared using any convenient methods, such as recombinant expression methods or synthetic methods, or purchased commercially. Screening of the D-peptidic compound may be performed using a cell-based assay, an enzyme assay, a ELISA assay, a surface plasmon resonance (SPR) binding assay or other convenient biological assay for assessing specific binding or the inhibition of binding.

In certain embodiments, the subject method includes: (i) contacting a sample containing a 40-mer or longer D-target protein with a 20-mer or longer L-peptidic library; (ii) determining whether a L-peptidic compound of the library specifically binds to the D-target protein; and (iii) producing the D-peptidic compound of the L-peptidic compound, if such a compound was identified. In certain embodiments, a L-peptidic binder is not identified after screening the D-protein target against a L-peptidic library.

Compositions

As summarized above, also provided are compositions for identifying D-peptidic compounds that specifically bind target proteins. In some embodiments, the composition includes a 40-mer or longer D-target protein and a library of 20-mer or longer L-peptidic compounds. In certain embodiments, the 40-mer or longer D-target protein of the composition is selected from the corresponding L-protein group consisting of a hormone, a growth factor, a receptor, an enzyme, a cytokine, an osteoinductive factor, a colony stimulating factor and an immunoglobulin. In certain embodiments, the 40-mer or longer D-protein target is selected from the group consisting of a VEGF protein, a RANKL protein, a NGF protein, a TNF-alpha protein, a SH2 domain-containing protein, a SH3 domain containing protein, and an IgE protein.

In certain embodiments, each compound of the 20-mer or longer L-peptidic library includes a scaffold domain and a distinct variable domain that includes at least 5 mutations. In certain embodiments, the 20-mer or longer L-peptidic library is a phage display library.

Utility

The methods and D-peptidic compounds of the invention, e.g., as described above, find use in a variety of applications. Applications of interest include, but are not limited to: therapeutic applications, research applications, and screening applications.

Therapeutic applications of interest include applications where the activity of a target protein is the cause or a compounding factor in disease progression. As such, the D-peptidic compounds of the subject methods find use in the treatment of a variety of different conditions in which the modulation of L-target protein activity in the host is desired. Examples of disease conditions include, but are not limited to: cancer, inhibition of angiogenesis and metastasis, osteoarthritis pain, chronic lower back pain, cancer-related pain, age-related macular degeneration (AMD), diabetic macular edema (DME), lymphangioleiomyomatosis (LAM), Ideopathic pulmonary fibrosis (IPF), and graft survival of transplanted corneas. In some cases, the disease condition is a target-mediated condition where the target is selected from the group consisting of a VEGF protein, a RANKL protein, a NGF protein, a TNF-alpha protein, a SH2 domain containing protein, a SH3 domain containing protein, an IgE protein, a BLyS protein, a PCSK9 protein, an Ang2 (Angiopoietin-2) protein, and a *Clostridium difficile* Toxin A or B protein.

The D-peptidic compounds of the subject methods find use in a variety of research applications. For example, analyzing the roles of target proteins in modulating various biological processes, including but not limited to, angiogenesis, inflammation, cellular growth, metabolism, regulation of transcription and regulation of phosphorylation. Other molecules such as antibodies that bind target proteins have found use in similar areas of biological research. See e.g., Sidhu and Fellhouse, "Synthetic therapeutic antibodies," Nature Chemical Biology, 2006, 2(12), 682-688.

Diagnostic applications include but are not limited to, the development of clinical diagnostics, e.g., in vitro diagnostics or in vivo tumor imaging agents. The D-peptidic compounds find use in diagnosing or confirming diagnosis of a disease condition, or susceptibility thereto. The D-peptidic compounds are also useful in methods for monitoring disease progression and/or response to treatment in patients who have been previously diagnosed with the disease. Diagnostic applications of interest include diagnosis of disease conditions, such as but not limited to: cancer, inhibition of angiogenesis and metastasis, osteoarthritis pain, chronic lower back pain, cancer-related pain, age-related macular degeneration (AMD), diabetic macular edema (DME), LAM: lymphangioleiomyomatosis, IPF: Ideopathic pulmonary fibrosis and graft survival of transplanted corneas. In some cases, the disease condition is a target-mediated condition where the target is selected from the group consisting of a VEGF protein, a RANKL protein, a NGF protein, a TNF-alpha protein, a SH2 domain containing protein, a SH3 domain containing protein, a Src protein, an IL-4 protein, an IL-8 protein, an IgE protein and fragments thereof. Molecules that bind target proteins, such as aptamers and antibodies, have previously found use as clinical diagnostic reagents, see for example, Jayasena, "Aptamers: An Emerging Class of Molecules That Rival Antibodies in Diagnostics," Clinical Chemistry. 1999; 45: 1628-1650.

The subject methods, e.g., as described above, find use in a variety of applications, including the production of D-peptidic compounds for a wide range of research and therapeutic applications, such as lead identification and affinity maturation, identification of diagnostic reagents, development of high throughput screening assays, development of drug delivery systems for the delivery of toxins or other therapeutic moieties. The subject methods may be exploited in multiple settings. The screening of peptide libraries has found use in the development of lead D-peptides as therapeutic agents, see Welch et al., "Potent D-peptide inhibitors of HIV-1 entry," PNAS, 2007, 104(43), 16828-16833.

The following examples are offered by way of illustration and not by way of limitation.

EXPERIMENTAL

1. Synthesis and Folding of D-VEGF Target Protein

D-VEGF was synthesized utilizing standard solid phase peptide synthesis and native chemical ligation methods (see e.g., review by Ackrill et al., Biopolymers (Pept Sci) 94: 495-503, 2010). The following fragments of D-VEGF were prepared (may also be referred to as D-VEGF(8-109)):

```
                                              (SEQ ID NO: 2)
1.   GQNHHEVVKFMDVYQRSY-SR (1-18);

(SEQ ID NO: 3)
2.   Thz-CHPIETLVDIFQEYPDEIEYIFKPSCVPLMR-SR (19-49)

(SEQ ID NO: 4)
3.   CGGCCNDEGLECVPTEESNITMQIMRIKPHQGQHIGEMSFLQHNKC
     ECRPKKD (50-102),
``` where SR refers to a C-terminal thioester and Thz is a protected form of Cys (Thz=1,3-thiazolidine-4-carboxo-).

Figure 9:
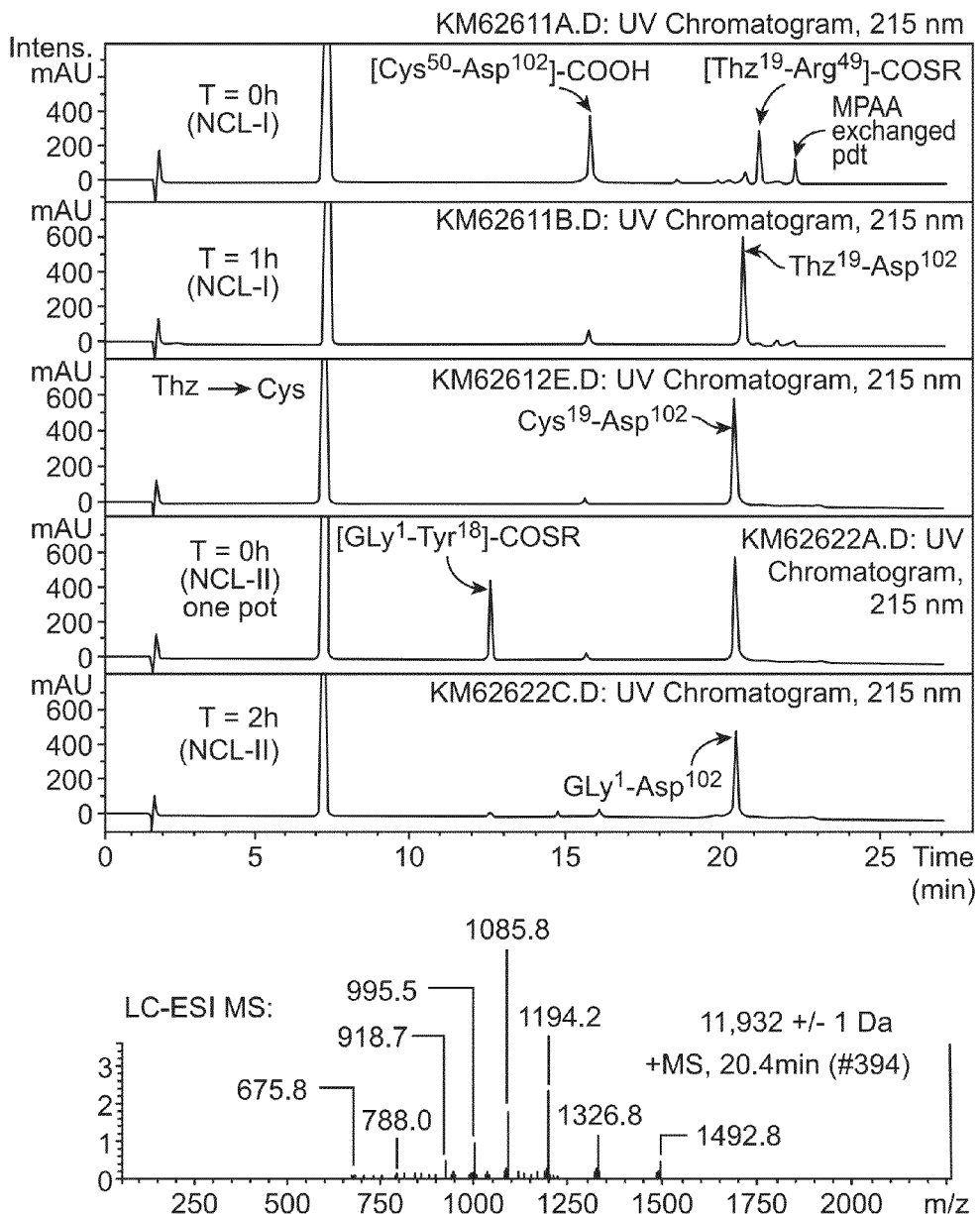
FIG. 9 shows LC-MS data from the synthesis of D-VEGF. RP-HPLC chromatograms (top) illustrate each step in the synthesis of D-VEGF. Also shown (bottom) is ESI MS data for the product.
Figure 11:
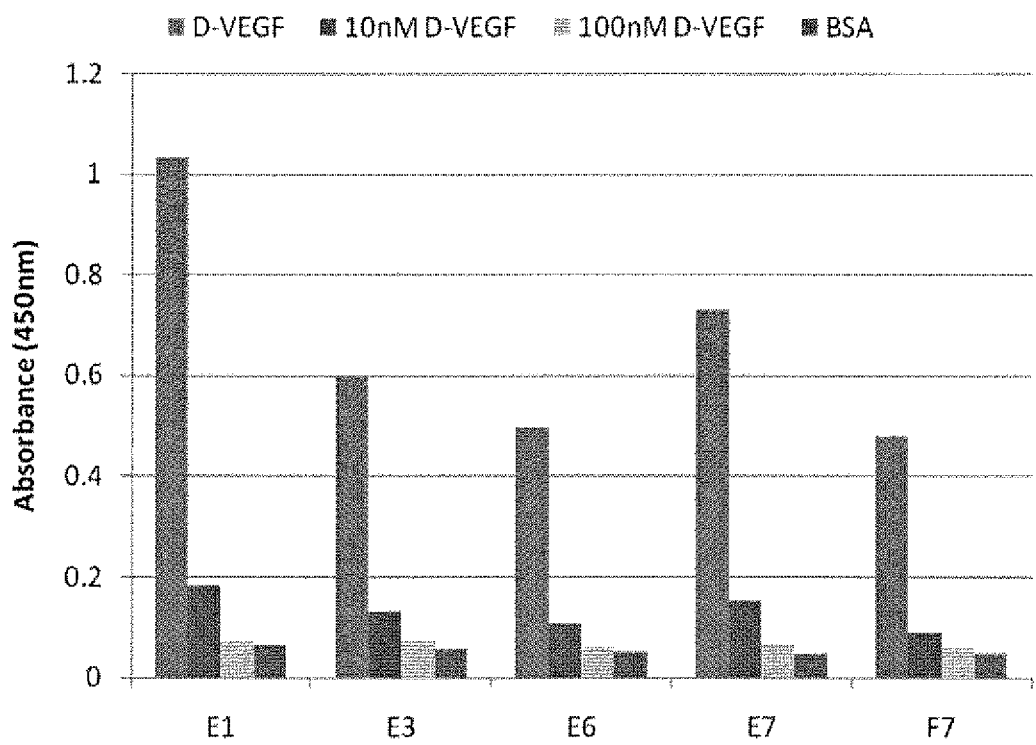
FIG. 11 illustrates binding assay results of individual clones identified from phage display screening of exemplary libraries 1-6 of FIG. 2 against D-VEGF. 10 nM or 100 nM D-VEGF protein was added to binding solutions in a competition binding assay.

Native chemical ligation methods were used to assemble the fragments as follows: fragments 2 and 3 were ligated to generate fragment (19-102) (NCL-I); the N-terminal cysteine of fragment (19-102) was deprotected (i.e. Thz- was converted to Cys-); and fragment 1 and fragment (Cys19-102) (NCL-II) were ligated to generate the 102 amino acid residue polypeptide D-VEGF. FIG. 9 shows RP-HPLC chromatograms (top) that illustrate each step in the synthesis of the polypeptide D-VEGF (8-109). At bottom of FIG. 9 is shown ESI MS data for the product (11,932+/−1 Da).

The synthetic D-VEGF was folded by incubating the protein in an aqueous buffer for 3 days (e.g., under the following conditions [VEGF]=0.5 mg/mL, [Glutathione]red=1.95 M, [Glutathione]ox=0.39 M, Tris=0.1 M, Gu.HCl=0.15 M, pH=8.4). FIG. 10 (top) illustrates LC chromatograms following the folding of the protein in solution after 0 hours, 1 day and 3 days. FIG. 10 (bottom) shows the LC chromatogram and direct infusion ESI MS data for purified, folded D-VEGF (observed mass: 23,849.2±0.5 Da, calculated mass: 23,849.1 Da (average isotopes)).

2. Phage Display of GB1 Peptidic Libraries 2.1 Cloning

The wild-type sequence of the Protein G B1 domain (Gronenborn et al., Science 253, 657-61, 1991) was prepared (Genscript USA Inc.) with an N-terminal FLAG tag and a C-terminal 10×His tag spaced by a Glycine-Glycine-Serine linker, is shown below:

```
                                              (SEQ ID NO: 5)
DYKDDDDK-GGS-TYKLILNGKTLKGETTTEAVDAATAEKVFKQYANDNG
VDGEWTYDDATKTFTVTE-GGS-HHHHHHHHHH-amber stop
```

This sequence was synthesized with NcoI and XbaI restriction sites at 5' and 3' respectively and cloned into a display vector as an N-terminal fusion to truncated protein 3 of M13 filamentous phage. The features of the vector include a ptac promoter and StII secretion leader sequence (MKKNIAFLLASMFVFSIATNAYA; SEQ ID NO: 6). This display version allows the display of GB1 in amber suppressor bacterial strains and is useful for expression of the protein in non-suppressor strains.

2.2 Optimization of Phage Display Levels

The presence of the His-tag and amber-stop at the C-terminus of the protein allows the purification of proteins/mutants without additional mutagenesis. In addition, to optimize for display of GB1 peptidic compounds, two additional constructs were tested for display-levels of GB1 (i) without His-tag and amber-stop (ii) with a hinge and dimerization sequence derived from a Fab-template (DKTHTCGRP; SEQ ID NO: 7) for dimeric display.

The following oligonucleotides were prepared (Integrated DNA Technologies Inc.), for site-directed mutagenesis:

```
i) 5'-GTT ACC GAA GGC GGT TCT TCT AGA AGT GGT TCC GGT-3'    SEQ ID NO: 8
        V   T   E   G   G   S   S   R   S   G   S   G       SEQ ID NO: 9
```

For removal of 10×His and amber-stop

```
ii)
5'-TT ACC GAA GGC GGT TCT GAC AAA ACT CAC ACA TGC GGC CGG CCC AGT GGT TCC GGT GAT T-3'    SEQ ID NO: 10
    V   T   E   G   G   S   D   K   T   H   T   C   G   R   P   S   G   S   G   D   F     SEQ ID NO: 11
```

For insertion of Fab-dimerization sequence to replace His-tag and amber stop

Site-directed mutagenesis was performed by methods described by Kunkel et al. (Methods Enzymol., 1987, 154, 367-82) and the sequence was confirmed by DNA sequencing. For comparing display levels, phage for each construct was harvested from a 25 mL overnight culture using methods described previously (Fellouse & Sidhu, "Making antibodies in bacteria. Making and using antibodies" Howard & Kaser, Eds., CRC Press, Boca Raton, Fla., 2007). The phage concentrations were estimated using a spectrophotometer ($OD_{268}$=1 for $5 \times 10^{12}$ phage/ml) and normalized to the lowest concentration. Three-fold serial dilutions of phage for each construct were prepared and added to NUNC maxisorb plates previously coated with anti-FLAG antibody (5 μg/ml) and blocked with BSA (0.2% BSA in PBS). The plates were washed and assayed with anti-M13-HRP to detect binding. The HRP signal was plotted as function of phage concentration.

2.3 Preparation of GB1 Peptidic Libraries

The solvent accessible surface area (SASA) for each residue in the Protein Data Bank (PDB) structure 3GB1 was estimated using the GETarea tool (Fraczkiewicz & Braun, "Exact and efficient analytical calculation of the accessible surface areas and their gradients for macromolecules," J. Comput. Chem. 1998, 19, 319-333). This tool also calculates the ratio of SASA in structure compared to SASA in a random coil. A ratio of 0.4 was used to identify solvent exposed residues (shown in bold):

```
                                            (SEQ ID NO: 1)
TYKLILNGKTLKGETTTEAVDAATAEKVFKQYANDNGVDGEWTYDDATKT

FTVTE.
```

Various contiguous stretches of solvent-accessible residues were selected for randomization (shown in red in FIGS. 3 to 8) taking into account the oligonucleotide length and homology requirements for Kunkel mutagenesis. The parent sequence is also shown in FIG. 2 with the numbering scheme and loop/beta-turn regions defined.

In addition, positions in the loops were selected for mutations that include insertion of 0, 1 or 2 additional amino acid residues in addition to substitution. Library 1: +0-2 insertions at position 38; Library 2: +0-2 insertions at position 19; Library 3: +2 insertions at position 1, +0-2 insertions at positions 19 and 47; Library 4: +0-2 insertions at positions 9 and 38, +1 insertion at position 55; Library 5: +0-2 insertions at position 9, +1 insertion at position 55; Library 6: +1 insertion at position 1, +0-2 insertions at position 47.

The following oligonucleotides were prepared (Integrated DNA Technologies) to make the libraries using the Kunkel mutagensis method:

Library 1:

```
                                           (SEQ ID NO: 12)
5'-ACGACCGAAGCAGTG KHT KHT KHT KHT GCA KHT KHT GTT
TTC KHT KHT TAC GCC KHT KHT AAT KHT KHT KHT KHT
KHT TGGACCTACGATGAT-3'

(SEQ ID NO: 13)
5'-ACGACCGAAGCAGTG KHT KHT KHT KHT GCA KHT KHT GTT
TTC KHT KHT TAC GCC KHT KHT AAT KHT KHT KHT KHT
KHT KHT TGGACCTACGATGAT-3'

(SEQ ID NO: 14)
5'-ACGACCGAAGCAGTG KHT KHT KHT KHT GCA KHT KHT GTT
TTC KHT KHT TAC GCC KHT KHT AAT KHT KHT KHT KHT
KHT KHT KHT TGGACCTACGATGAT-3'
```

These oligonucleotides include the variable regions where each variant amino acid position is encoded by a KHT codon. SEQ ID NOs: 12-14 include mutations of +0, 1 or 2 additional variant amino acids, respectively, at the position equivalent to position 38 of the scaffold.

Library 2:

```
                                           (SEQ ID NO: 15)
5'-GGTGAAACCACGACC KHT KHT KHT KHT KHT KHT KHT GCA
KHT KHT KHT TTC KHT KHT KHT GCC KHT KHT AATGGCGTGG
ATGGT-3'

(SEQ ID NO: 16)
5'-GGTGAAACCACGACC KHT KHT KHT KHT KHT KHT KHT KHT
GCA KHT KHT KHT TTC KHT KHT KHT GCC KHT KHT AATGGC
GTGGATGGT-3'

(SEQ ID NO: 17)
5'-GGTGAAACCACGACC KHT KHT KHT KHT KHT KHT KHT KHT
KHT GCA KHT KHT KHT TTC KHT KHT KHT GCC KHT KHT
AATGGCGTGGATGGT-3'
```

These oligonucleotides include the variable regions where each variant amino acid position is encoded by a KHT codon. SEQ ID NOs: 15-17 include insertion mutations of +0, 1 or 2 additional variant amino acids, respectively, at the position equivalent to position 19 of the scaffold.

Library 3:

```
                                           (SEQ ID NO: 18)
5'-GATGATAAAGGCGGTAGC KHT KHT KHT TACAAACTGATTCTGA
AC-3'

(SEQ ID NO: 19)
5'-AAAGGTGAAACCACGACC KHT KHT KHT KHT KHT KHT KHT
GCAGAAAAAGTTTTCAAA-3'

(SEQ ID NO: 20)
5'-AAAGGTGAAACCACGACC KHT KHT KHT KHT KHT KHT KHT
KHT GCAGAAAAAGTTTTCAAA-3'

(SEQ ID NO: 21)
5'-AAAGGTGAAACCACGACC KHT KHT KHT KHT KHT KHT KHT
KHT KHT GCAGAAAAAGTTTTCAAA-3'

(SEQ ID NO: 22)
5'-GATGGTGAATGGACCTAC KHT KHT KHT KHT KHT ACCTTCAC
GGTTACCGAA-3'

(SEQ ID NO: 23)
5'-GATGGTGAATGGACCTAC KHT KHT KHT KHT KHT KHT ACCT
TCACGGTTACCGAA-3'

(SEQ ID NO: 24)
5'-GATGGTGAATGGACCTAC KHT KHT KHT KHT KHT KHT KHT
ACCTTCACGGTTACCGAA-3'
```

These oligonucleotides include the variable regions where each variant amino acid position is encoded by a KHT codon. SEQ ID NO: 18 includes an insertion mutation of +2 variant amino acids at the position equivalent to position 1 of the scaffold. SEQ ID NOs: 19-21 include mutations of +0, 1 or 2 additional variant amino acids, respectively, at the position equivalent to position 19 of the scaffold. SEQ ID NOs: 22-24 include mutations of +0, 1 or 2 additional variant amino acids, respectively, at the position equivalent to position 47 of the scaffold.

Library 4

(SEQ ID NO: 25)
5'-ACGTACAAACTGATTCTG KHT KHT KHT KHT KHT KHT GGTG
AAACCACGACCGAA-3'

(SEQ ID NO: 26)
5'-ACGTACAAACTGATTCTG KHT KHT KHT KHT KHT KHT KHT
GGTGAAACCACGACCGAA-3'

(SEQ ID NO: 27)
5'-ACGTACAAACTGATTCTG KHT KHT KHT KHT KHT KHT KHT
KHT GGTGAAACCACGACCGAA-3'

(SEQ ID NO: 28)
5'-AAACAGTACGCCAACGAT KHT KHT KHT KHT KHT KHT TGGA
CCTACGATGATGCG-3'

(SEQ ID NO: 29)
5'-AAACAGTACGCCAACGAT KHT KHT KHT KHT KHT KHT KHT
TGGACCTACGATGATGCG-3'

(SEQ ID NO: 30)
5'-AAACAGTACGCCAACGAT KHT KHT KHT KHT KHT KHT KHT
KHT TGGACCTACGATGATGCG-3'

(SEQ ID NO: 31)
5'-ACGAAAACCTTCACGGTT KHT KHT KHT GGCGGTTCTGACAAAA
CT-3'

These oligonucleotides include the variable regions where each variant amino acid position is encoded by a KHT codon. SEQ ID NOs: 25-27 include mutations of +0, 1 or 2 additional variant amino acids, respectively, at the position equivalent to position 9 of the scaffold. SEQ ID NOs: 28-30 include mutations of +0, 1 or 2 additional variant amino acids, respectively, at the position equivalent to position 38 of the scaffold. SEQ ID NO: 31 includes an insertion mutation of +2 variant amino acids at the position equivalent to position 55 of the scaffold.

Library 5

(SEQ ID NO: 32)
5'-AAAGGCGGTAGCACGTAC KHT CTG KHT CTG KHT KHT KHT
KHT KHT KHT KHT KHT ACC KHT ACCGAAGCAGTGGATGCA-3'

(SEQ ID NO: 33)
5'-AAAGGCGGTAGCACGTAC KHT CTG KHT CTG KHT KHT KHT
KHT KHT KHT KHT KHT KHT ACC KHT ACCGAAGCAGTGGATGC
A-3'

(SEQ ID NO: 34)
5'-AAAGGCGGTAGCACGTAC KHT CTG KHT CTG KHT KHT KHT
KHT KHT KHT KHT KHT KHT ACC KHT ACCGAAGCAGTGGA
TGCA-3'

(SEQ ID NO: 35)
5'-GATGCGACGAAAACCTTC KHT GTT KHT KHT KHT GGCGGTTC
TGACAAAACT-3'

These oligonucleotides include the variable regions where each variant amino acid position is encoded by a KHT codon. SEQ ID NOs: 32-34 include mutations of +0, 1 or 2 additional variant amino acids, respectively, at the position equivalent to position 9 of the scaffold. SEQ ID NO: 35 includes an insertion mutation of +2 variant amino acids at the position equivalent to position 55 of the scaffold.

Library 6

(SEQ ID NO: 36)
5'-GATGATAAAGGCGGTAGC KHT KHT TAC KHT CTG KHT CTG
KHT GGCAAAACCCTGAAAGGT-3'

(SEQ ID NO: 37)
5'-GATAATGGCGTGGATGGT KHT TGG KHT TAC KHT KHT KHT
KHT KHT KHT TTC KHT GTT KHT GAAGGCGGTTCTGACAAA-3'

(SEQ ID NO: 38)
5'-GATAATGGCGTGGATGGT KHT TGG KHT TAC KHT KHT KHT
KHT KHT KHT KHT TTC KHT GTT KHT GAAGGCGGTTCTGACAA
A-3'

(SEQ ID NO: 39)
5'-GATAATGGCGTGGATGGT KHT TGG KHT TAC KHT KHT KHT
KHT KHT KHT KHT KHT TTC KHT GTT KHT GAAGGCGGTTCTG
ACAAA-3'

These oligonucleotides include the variable regions where each variant amino acid position is encoded by a KHT codon. SEQ ID NO: 36 includes an insertion mutation of +1 variant amino acids at the position equivalent to position 1 of the scaffold. SEQ ID NOs: 37-38 include mutations of +0, 1 or 2 additional variant amino acids, respectively, at the position equivalent to position 47 of the scaffold.

The libraries were prepared using the same method described above for the GB1 template with Fab dimerization sequence (Fellouse & Sidhu, 2007). Oligonucleotides with 0/1/2 insertions have the same homology regions and compete for binding the template. Therefore they were pooled together (equimolar ratio) and treated as a single oligonucleotide for mutagenesis. The constructed libraries were pooled together for total diversity of $3.5 \times 10^{10}$ transformants.

3. Methods of Screening of Phage Display Libraries 3.1 Library Selections Against D-Target Protein and Negative selection with BSA The selection procedure is essentially the same as described in previous protocols (Fellouse & Sidhu, 2007) with some minor changes. Although the method below is described for D-VEGF, the method can be adapted to screen for binding to any target. The media and buffer recipes are the same as in the described protocol. Phage display libraries 1 to 6 prepared as described above were selected for binding to D-VEGF according to the following method.

1. Coat NUNC Maxisorb plate wells with 100 µl of D-VEGF (5 µg/ml in PBS) for 2 h at room temperature. Coat 5 wells for selection and 1 well for phage pool ELISA.

2. Remove the coating solution and block for 1 h with 200 µl of PBS, 0.2% BSA. At the same time, block an uncoated well as a negative control for pool ELISA. Also block 7 wells for pre-incubation of library on a separate plate.

3. Remove the block solution from the pre-incubation plate and wash four times with PT buffer.

4. Add 100 µl of library phage solution (precipitated and resuspended in PBT buffer) to each blocked wells. Incubate at room temperature for 1 h with gentle shaking.

5. Remove the block solution from selection plate and wash four times with PT buffer.

6. Transfer library phage solution from pre-incubation plate to selection plate (5 selection wells+2 controls for pool ELISA)

7. Remove the phage solution and wash 8-10 times with PT buffer (increased based pool ELISA signal from previous round).

8. To elute bound phage from selection wells, add 100 µl of 100 mM HCl. Incubate 5 min at room temperature. Transfer the HCl solution to a 1.5-ml microfuge tube. Adjust to neutral pH with 11 µl of 1.0 M Tris-HCl, pH 11.0.

9. In the meantime add 100 µl of anti-M13 HRP conjugate (1:5000 dilution in PBT buffer) to the control wells and incubate for 30 min.
10. Wash control wells four times with PT buffer. Add 100 µl of freshly prepared TMB substrate. Allow color to develop for 5-10 min.
11. Stop the reaction with 100 µl of 1.0 M $H_3PO_4$ and read absorbance at 450 nm in a microtiter plate reader. The enrichment ratio can be calculated as the ratio of signal from coated vs uncoated well.
12. Add 250 µl eluted phage solution to 2.5 ml of actively growing E. coli XL1-Blue ($OD_{600}$<0.8) in 2YT/tet medium. Incubate for 20 min at 37° C. with shaking at 200 rpm.
13. Add M13KO7 helper phage to a final concentration of $10^{10}$ phage/ml. Incubate for 45 min at 37° C. with shaking at 200 rpm.
14. Transfer the culture from the antigen-coated wells to 25 volumes of 2YT/carb/kan medium and incubate overnight at 37° C. with shaking at 200 rpm.
15. Isolate phage by precipitation with PEG/NaCl solution, resuspend in 1.0 ml of PBT buffer
16. Repeat the selection cycle for 4 rounds.
3.2. Negative Selection with GST Tagged Protein
A more stringent negative selection procedure is as follows. The selection process is essentially the same as described above except that:
i) For Rounds 1 and 2 the libraries were pre-incubated on GST coated (10 µg/ml in PBS) and blocked wells.
ii) For Rounds 3 and 4, the libraries were pre-incubated with 0.2 mg/ml GST in solution for 1 hr before transfer to selection wells
iii) The control wells for pool ELISA were coated with GST (5 µg/ml in PBS)

4. Analysis of Single-Clones by Direct Binding ELISA

The following protocol is an adapted version of previous protocols (Fellouse & Sidhu 2007; Tonikian et al., "Identifying specificity profiles for peptide recognition modules from phage-displayed peptide libraries," Nat. Protoc., 2007, 2, 1368-86), and was used to analyse clones identified by selection of Libraries 1 to 6 against D-VEGF described above:
1. Inoculate 450 µl aliquots of 2YT/carb/KO7 medium in 96-well microtubes with single colonies harboring phagemids and grow for 21 hrs at 37° C. with shaking at 200 rpm.
2. Centrifuge at 4,000 rpm for 10 min and transfer phage supernatants to fresh tubes.
3. Coat 3 wells of a 384 well NUNC maxisorb plate per clone, with 2 µg/ml of D-VEGF, Neutravidn, Erbin-GST respectively and leave one well uncoated. Incubate for 2 hrs at room temperature and block the plates (all 4 well).
4. Wash the plate four times with PT buffer.
5. Transfer 30 µl of phage supernatant to each well and incubate for 2 hrs at room temperature with gentle shaking.
6. Wash four times with PT buffer.
7. Add 30 µl of anti-M13-HRP conjugate (diluted 1:5000 in PBT buffer). Incubate 30 min with gentle shaking.
8. Wash four times with PT buffer
9. Add 30 µl of freshly prepared TMB substrate. Allow color to develop for 5-10 min.
10. Stop the reaction with 100 µl of 1.0 M $H_3PO_4$ and read absorbance at 450 nm in a microtiter plate reader.

5. Binding Affinity by SPR

Binding affinities were measured using the Biacore SPR system. SPR analysis was performed on a ProteOn XPR36 Protein Interaction Array System (BioRad). Chemically synthesized L-VEGF, D-VEGF and VEGF165 (Peprotech) were immobilized in 50 mM Sodium Acetate (pH 5.5) to a non-dilute EDAC/sulfo-NHS activated GLC surface on separate channels using a flow rate of 30 ml/min for 5 minutes in the vertical direction. Immobilization levels were monitored to ensure immobilization of approximately 500 response units of each protein. The domains were then stabilized with PBS for 30 seconds and 0.85% H3PO4 for 18 seconds each at 100 ml/min.

VEGF-binding compounds were diluted in PBS plus 0.05% Tween 20 at a starting concentration of 200 nM. The binders were further diluted with PBST 2-fold in series to produce 5 concentrations of compounds. A PBST blank was also included. The injection parameters were: 100 ml/min, 60 seconds contact time, and 600 seconds dissociation time, in the horizontal direction. VEGF proteins were regenerated with an injection of 0.85% $H_3PO_4$ at a flow rate of 100 ml/min followed by a PBST wash of 30 seconds at 100 ml/min flow rate.

TABLE 1

SPR affinity measurements of VEGF binding peptidic compounds

| Clone | Target | $K_{on}$ ($M^{-1}s^{-1}$) | $K_{off}$ ($s^{-1}$) | Affinity (nM) |
|---|---|---|---|---|
| E01 | L-VEGF | x | x | x |
|  | VEGF165 | x | x | x |
|  | D-VEGF | 2.60E+05 | 3.47E−03 | 13.4 |
| E01-V22L | L-VEGF | x | x | x |
|  | VEGF165 | x | x | x |
|  | D-VEGF | 4.11E+05 | 2.39E−03 | 5.8 |
| E01-Y23F (AM1) | L-VEGF | x | x | x |
|  | VEGF165 | x | x | x |
|  | D-VEGF | 3.98E+05 | 2.91E−03 | 7.3 |
| E01-D24G | L-VEGF | x | x | x |
|  | VEGF165 | x | x | x |
|  | D-VEGF | 1.66E+05 | 2.47E−03 | 14.9 |
| E01-D27E | L-VEGF | x | x | x |
|  | VEGF165 | x | x | x |
|  | D-VEGF | 3.47E+05 | 3.33E−03 | 9.6 |
| E01-V31A | L-VEGF | x | x | x |
|  | VEGF165 | x | x | x |
|  | D-VEGF | 2.50E+05 | 1.94E−03 | 7.8 |
| E01-A34S | L-VEGF | x | x | x |
|  | VEGF165 | x | x | x |
|  | D-VEGF | 3.56E+05 | 2.78E−03 | 7.8 |
| E01-S35R | L-VEGF | x | x | x |
|  | VEGF165 | x | x | x |
|  | D-VEGF | 2.79E+05 | 2.58E−03 | 9.3 |
| E01-S35E | L-VEGF | x | x | x |
|  | VEGF165 | x | x | x |
|  | D-VEGF | 4.07E+05 | 3.04E−03 | 7.47 |
| E01-S35G | L-VEGF | x | x | x |
|  | VEGF165 | x | x | x |
|  | D-VEGF | 3.96E+05 | 3.48E−03 | 8.79 |
| E01-S38K | L-VEGF | x | x | x |
|  | VEGF165 | x | x | x |
|  | D-VEGF | 2.04E+05 | 2.80E−03 | 13.7 |
| E01-S38G | L-VEGF | x | x | x |
|  | VEGF165 | x | x | x |
|  | D-VEGF | 4.28E+05 | 3.87E−03 | 9 |
| E01-D39F | L-VEGF | x | x | x |
|  | VEGF165 | x | x | x |
|  | D-VEGF | 5.04E+05 | 2.13E−03 | 4.23 |
| E01-F40I | L-VEGF | x | x | x |
|  | VEGF165 | x | x | x |
|  | D-VEGF | 3.98E+05 | 4.41E−03 | 11.1 |
| E01-D41V | L-VEGF | x | x | x |
|  | VEGF165 | x | x | x |
|  | D-VEGF | 4.93E+05 | 3.33E−02 | 67.5 |

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   a) contacting a 50 residue or more D-target protein with a library of 50 residue or more distinct β1 domain of Protein G (GB1) L-peptidic compounds comprising a 4β-1α structural motif, wherein the compounds of the library are described by the formula β1-β2-α1-β3-β4 wherein β1, β2, β3 and β4 are independently beta-strand domains; and β1, β2, α1, β3, β4 are connected independently by linking sequences of between 1 and 10 residues in length, wherein the compounds of the library have at least 8 mutations outside of the β1-β2 and β3-β4 regions, wherein the compounds of the library have at least 10 conserved residues in the β1-β2 and β3-β4 regions, wherein the library is a phage display library, wherein the compounds of the library comprise between 20 and 80 residues;
   b) identifying a L-peptidic compound of the library that specifically binds to the D-target protein; and
   c) producing the D-peptidic compound of the identified L-peptidic compound.

2. The method according to claim 1, wherein the 50 residue or more D-target protein is selected from the group consisting of a hormone, a growth factor, a receptor, an enzyme, a cytokine, an osteoinductive factor, a colony stimulating factor and an immunoglobulin.

3. The method according to claim 2, wherein the 50 residue or more D-target protein is selected from the group consisting of a growth hormone, a bovine growth hormone, an insulin like growth factor, a human growth hormone, a parathyroid hormone, a proinsulin, a prorelaxin, a glycoprotein hormone, a leutinizing hormone, a hemapoietic growth factor, a fibroblast growth factor, a prolactin, a placental lactogen, a tumor necrosis factor, a mullerian inhibiting substance, an inhibin, an activin, a VEGF protein, an integrin, a RANKL protein, a NGF protein, an insulin-like growth factor-I or II, an erythropoietin, an osteoinductive factor, an interferon, a colony stimulating factor, an interleukin, an IgE protein, a bone morphogenetic protein, LIF, a SCF protein, kit-ligand, a SH2 domain containing protein, a SH3 domain containing protein, an IL-4 protein, an IL-8 protein, an apoptosis protein, a hepatocyte growth factor, a hepatocyte growth factor receptor, neutravidin, and a maltose binding protein.

4. The method according to claim 3, wherein the D-target protein is selected from the group consisting of a VEGF protein, a RANKL protein, a NGF protein, a TNF-alpha protein, a 3BP2 protein, an ABL protein, a Src protein, an IgE protein, a BLyS protein, a PCSK9 protein, an Ang2 protein, and a *Clostridium difficile* Toxin A or B protein.

5. The method according to claim 1, wherein the compounds of the library comprise between 30 and 80 residues.

6. The method according to claim 5, wherein the compounds of the library comprise between 40 and 70 residues.

7. The method according to claim 6, wherein the compounds of the library comprise between 45 and 60 residues.

8. The method according to claim 7, wherein the compounds of the library comprise between 52 and 58 residues.

9. The method according to claim 1, wherein the D-target protein comprises 75 or more residues.

10. The method according to claim 9, wherein the D-target protein comprises 100 or more residues.

11. The method according to claim 10, wherein the D-target protein comprises 125 or more residues.

12. The method according to claim 11, wherein the D-target protein comprises 150 or more residues.

13. The method according to claim 12, wherein the D-target protein comprises 175 or more residues.

14. The method according to claim 13, wherein the D-target protein comprises 200 or more residues.

15. The method according to claim 1, wherein the compounds of the library comprise a scaffold domain and a variable domain that comprises at least 10 mutations.

16. The method according to claim 15, wherein the variable domain comprises at least 14 mutations.

17. The method according to claim 1, further comprising screening the D-peptidic compound for specific binding to the L-enantiomer of the D-target protein.

* * * * *

```
                        SEQUENCE LISTING

<160> NUMBER OF SEQ ID NOS: 52

<210> SEQ ID NO 1
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 1

Thr Tyr Lys Leu Ile Leu Asn Gly Lys Thr Leu Lys Gly Glu Thr Thr
 1               5                  10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 2
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 2

Gly Gln Asn His His Glu Val Val Lys Phe Met Asp Val Tyr Gln Arg
 1               5                  10                  15

Ser Tyr

<210> SEQ ID NO 3
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 3

Cys His Pro Ile Glu Thr Leu Val Asp Ile Phe Gln Glu Tyr Pro Asp
 1               5                  10                  15

Glu Ile Glu Tyr Ile Phe Lys Pro Ser Cys Val Pro Leu Met Arg
            20                  25                  30

<210> SEQ ID NO 4
<211> LENGTH: 53
<212> TYPE: PRT
<213> ORGANISM: Artificial Sequence
<220> FEATURE:
<223> OTHER INFORMATION: Synthetic polypeptide
```

<400> SEQUENCE: 4

Cys Gly Gly Cys Cys Asn Asp Glu Gly Leu Glu Cys Val Pro Thr Glu
1               5                   10                  15

Glu Ser Asn Ile Thr Met Gln Ile Met Arg Ile Lys Pro His Gln Gly
            20                  25                  30

Gln His Ile Gly Glu Met Ser Phe Leu Gln His Asn Lys Cys Glu Cys
        35                  40                  45

Arg Pro Lys Lys Asp
    50

<210> SEQ ID NO 5
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 5

Asp Tyr Lys Asp Asp Asp Lys Gly Gly Ser Thr Tyr Lys Leu Ile
1               5                   10                  15

Leu Asn Gly Lys Thr Leu Lys Gly Glu Thr Thr Thr Glu Ala Val Asp
            20                  25                  30

Ala Ala Thr Ala Glu Lys Val Phe Lys Gln Tyr Ala Asn Asp Asn Gly
        35                  40                  45

Val Asp Gly Glu Trp Thr Tyr Asp Asp Ala Thr Lys Thr Phe Thr Val
    50                  55                  60

Thr Glu Gly Gly Ser His His His His His His His His
65                  70                  75

<210> SEQ ID NO 6
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 6

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Asp Lys Thr His Thr Cys Gly Arg Pro
1               5

<210> SEQ ID NO 8
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 8
gttaccgaag gcggttcttc tagaagtggt tccggt                                 36

<210> SEQ ID NO 9
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 9

Val Thr Glu Gly Gly Ser Ser Arg Ser Gly Ser Gly
 1               5                  10

<210> SEQ ID NO 10
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 10
ttaccgaagg cggttctgac aaaactcaca catgcggccg gcccagtggt tccggtgatt    60

<210> SEQ ID NO 11
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 11

Val Thr Glu Gly Gly Ser Asp Lys Thr His Thr Cys Gly Arg Pro Ser
 1               5                  10                  15

Gly Ser Gly Asp Phe
            20

<210> SEQ ID NO 12
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 12
acgaccgaag cagtgkhtkh tkhtkhtgca khtkhtgttt tckhtkhtta cgcckhtkht    60
aatkhtkhtk htkhtkhttg gacctacgat gat                                 93

<210> SEQ ID NO 13
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 13
acgaccgaag cagtgkhtkh tkhtkhtgca khtkhtgttt tckhtkhtta cgcckhtkht    60
aatkhtkhtk htkhtkhtkh ttggacctac gatgat                              96

<210> SEQ ID NO 14
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 14

```
acgaccgaag cagtgkhtkh tkhtkhtgca khtkhtgttt tckhtkhtta cgcckhtkht       60
aatkhtkhtk htkhtkhtkh tkhttggacc tacgatgat                              99
```

<210> SEQ ID NO 15
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 15

```
ggtgaaacca cgacckhtkh tkhtkhtkht khtkhtgcak htkhtkhttt ckhtkhtkht       60
gcckhtkhta atggcgtgga tggt                                             84
```

<210> SEQ ID NO 16
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 16

```
ggtgaaacca cgacckhtkh tkhtkhtkht khtkhtkhtg cakhtkhtkh tttckhtkht       60
khtgcckhtk htaatggcgt ggatggt                                          87
```

<210> SEQ ID NO 17
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 17

```
ggtgaaacca cgacckhtkh tkhtkhtkht khtkhtkhtk htgcakhtkh tkhtttckht       60
khtkhtgcck htkhtaatgg cgtggatggt                                       90
```

<210> SEQ ID NO 18
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 18

```
gatgataaag gcggtagckh tkhtkhttac aaactgattc tgaac                      45
```

<210> SEQ ID NO 19
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 19

```
aaaggtgaaa ccacgacckh tkhtkhtkht khtkhtkhtg cagaaaaagt tttcaaa         57
```

<210> SEQ ID NO 20
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 20
aaaggtgaaa ccacgacckh tkhtkhtkht khtkhtkhtk htgcagaaaa agttttcaaa    60

<210> SEQ ID NO 21
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 21
aaaggtgaaa ccacgacckh tkhtkhtkht khtkhtkhtk htkhtgcaga aaaagttttc    60
aaa                                                                 63

<210> SEQ ID NO 22
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 22
gatggtgaat ggacctackh tkhtkhtkht khtaccttca cggttaccga a             51

<210> SEQ ID NO 23
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 23
gatggtgaat ggacctackh tkhtkhtkht khtkhtacct tcacggttac cgaa          54

<210> SEQ ID NO 24
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 24
gatggtgaat ggacctackh tkhtkhtkht khtkhtkhta ccttcacggt taccgaa       57

<210> SEQ ID NO 25
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 25
acgtacaaac tgattctgkh tkhtkhtkht khtkhtggtg aaaccacgac cgaa          54

<210> SEQ ID NO 26
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 26
acgtacaaac tgattctgkh tkhtkhtkht khtkhtkhtg gtgaaaccac gaccgaa       57

```
<210> SEQ ID NO 27
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 27
acgtacaaac tgattctgkh tkhtkhtkht khtkhtkhtk htggtgaaac cacgaccgaa      60

<210> SEQ ID NO 28
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 28
aaacagtacg ccaacgatkh tkhtkhtkht khtkhttgga cctacgatga tgcg           54

<210> SEQ ID NO 29
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 29
aaacagtacg ccaacgatkh tkhtkhtkht khtkhtkhtt ggacctacga tgatgcg        57

<210> SEQ ID NO 30
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 30
aaacagtacg ccaacgatkh tkhtkhtkht khtkhtkhtk httggaccta cgatgatgcg     60

<210> SEQ ID NO 31
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 31
acgaaaacct tcacggttkh tkhtkhtggc ggttctgaca aaact                     45

<210> SEQ ID NO 32
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 32
aaaggcggta gcacgtackh tctgkhtctg khtkhtkhtk htkhtkhtkh tkhtacckht     60
accgaagcag tggatgca                                                  78

<210> SEQ ID NO 33
<211> LENGTH: 81
<212> TYPE: DNA
<213> ORGANISM: Artificial Sequence
<220> FEATURE:
```

<223> OTHER INFORMATION: Synthetic polynucleotide

<400> SEQUENCE: 33
aaaggcggta gcacgtackh tctgkhtctg khtkhtkhtk htkhtkhtkh tkhtkhtacc    60
khtaccgaag cagtggatgc a    81

<210> SEQ ID NO 34
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 34
aaaggcggta gcacgtackh tctgkhtctg khtkhtkhtk htkhtkhtkh tkhtkhtkht    60
acckhtaccg aagcagtgga tgca    84

<210> SEQ ID NO 35
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 35
gatgcgacga aaaccttckh tgttkhtkht khtggcggtt ctgacaaaac t    51

<210> SEQ ID NO 36
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 36
gatgataaag gcggtagckh tkhttackht ctgkhtctgk htggcaaaac cctgaaaggt    60

<210> SEQ ID NO 37
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 37
gataatggcg tggatggtkh ttggkhttac khtkhtkhtk htkhtkhttt ckhtgttkht    60
gaaggcggtt ctgacaaa    78

<210> SEQ ID NO 38
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 38
gataatggcg tggatggtkh ttggkhttac khtkhtkhtk htkhtkhtkh tttckhtgtt    60
khtgaaggcg gttctgacaa a    81

<210> SEQ ID NO 39
<211> LENGTH: 84
<212> TYPE: DNA
<213> ORGANISM: Artificial Sequence -continued

```
<220> FEATURE:
<223> OTHER INFORMATION: Synthetic polynucleotide

<400> SEQUENCE: 39
gataatggcg tggatggtkh ttggkhttac khtkhtkhtk htkhtkhtkh tkhtttckht      60
gttkhtgaag gcggttctga caaa                                            84

<210> SEQ ID NO 40
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 7, 9, 11, 12, 16, 18, 19, 20
<223> OTHER INFORMATION: X1 = T or S, X3 = K or R, X7 = N or K, X9 = K,
      N V or A, X11 = L or F, X12 = K or S, X16 = T or
      A or S, X18 = K or E, X19 = A or T, X20 = V or I
<221> NAME/KEY: VARIANT
<222> LOCATION: 22, 23, 24, 27, 28, 30, 31
<223> OTHER INFORMATION: X22 = A, T or V; X23 = A or E; X24 = T or V;
      X27 = K or Q; X28 = A, E, T or V; X30 = K or R; X31 = Q or D
<221> NAME/KEY: VARIANT
<222> LOCATION: 34, 35, 37, 39, 41, 43, 46
<223> OTHER INFORMATION: X34 = N or T; X35 = A, D, E or K; X37 =
      G or N; X39 = D or T; X41 = E or V; X43 = A, T or
      S; X46 = D, A, Y or T
<221> NAME/KEY: VARIANT
<222> LOCATION: 5, 6, 51, 53
<223> OTHER INFORMATION: X = hydrophobic
<221> NAME/KEY: VARIANT
<222> LOCATION: 38
<223> OTHER INFORMATION: X = non aromatic hydrophobic

<400> SEQUENCE: 40

Xaa Tyr Xaa Leu Xaa Xaa Xaa Gly Xaa Thr Xaa Xaa Gly Glu Thr Xaa
 1               5                  10                  15

Thr Xaa Xaa Xaa Asp Xaa Xaa Xaa Ala Glu Xaa Xaa Phe Xaa Xaa Tyr
            20                  25                  30

Ala Xaa Xaa Asn Xaa Xaa Xaa Gly Xaa Trp Xaa Tyr Asp Xaa Ala Thr
        35                  40                  45

Lys Thr Xaa Thr Xaa Thr Glu
    50                  55

<210> SEQ ID NO 41
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 5, 6, 7, 9, 11, 12, 16, 18, 19
<223> OTHER INFORMATION: X1 = T or S, X3 = K or R, X5 = I or V, X6 = L,
      I or V, X7 = N or K, X9 = K, N, V or A, X11 = L or
      F, X12 = K or S, X16 = T, A or S, X18 = K or E,
      X19 = A or T
<221> NAME/KEY: VARIANT
<222> LOCATION: 20, 22, 23, 24, 27, 28, 30, 31
<223> OTHER INFORMATION: X20 = V or I; X22 = A, T or V; X23 = A or E;
      X24 = T or V; X27 = K or Q; X28 = A, E, T or V; X30 = K
      or R; X31 = Q or D
<221> NAME/KEY: VARIANT
<222> LOCATION: 34, 35, 37, 38, 39, 41, 43, 46
<223> OTHER INFORMATION: X34 = N or T; X35 = A, D, E or K; X37 = G or
      N; X38 = V or I; X39 = D or T; X41 = E or V; X43 =
      A, T or S; X46 = D, A, Y or T

<400> SEQUENCE: 41

Xaa Tyr Xaa Leu Xaa Xaa Xaa Gly Xaa Thr Xaa Xaa Gly Glu Thr Xaa
 1               5                  10                  15
```

Thr Xaa Xaa Xaa Asp Xaa Xaa Xaa Ala Glu Xaa Xaa Phe Xaa Xaa Tyr
             20                  25                  30

Ala Xaa Xaa Asn Xaa Xaa Xaa Gly Xaa Trp Xaa Tyr Asp Xaa Ala Thr
         35                  40                  45

Lys Thr Phe Thr Val Thr Glu
     50                  55

<210> SEQ ID NO 42
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 5, 6, 7, 9, 11, 12, 16, 18, 22
<223> OTHER INFORMATION: X5 = I or V; X6 = L, I or V; X7 = N or K;
      X9 = N or K; X11 = L or F; X12 = K or S; X16 = T or A; X18 = K or
      E; X22 = A, T or V
<221> NAME/KEY: VARIANT
<222> LOCATION: 23, 27, 28, 30, 34, 35, 37, 41, 43, 46
<223> OTHER INFORMATION: X23 = A or E; X27 = K or Q; X28 = A, E, T or V;
      X30 = K or R; X34 = N or T; X35 = A, D, E or K;
      X37 = G or N; X41 = E or V; X43 = A, T or S; X46 =
      D or A

<400> SEQUENCE: 42

Thr Tyr Lys Leu Xaa Xaa Xaa Gly Xaa Thr Xaa Xaa Gly Glu Thr Xaa
 1               5                  10                  15

Thr Xaa Ala Val Asp Xaa Xaa Thr Ala Glu Xaa Xaa Phe Xaa Gln Tyr
             20                  25                  30

Ala Xaa Xaa Asn Xaa Val Asp Gly Xaa Trp Xaa Tyr Asp Xaa Ala Thr
         35                  40                  45

Lys Thr Phe Thr Val Thr Glu
     50                  55

<210> SEQ ID NO 43
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 7, 8, 9, 10, 11, 12, 13
<223> OTHER INFORMATION: X7 = N or V, X8 = G, L or I, X9 K or G, X10 =
      Q, T or D, X11 = L, A or R, X12 = K or V, X13 = G, E or V
<221> NAME/KEY: VARIANT
<222> LOCATION: 14, 15, 16, 17, 19, 23, 24
<223> OTHER INFORMATION: X14 = E or V, X15 = A, T, R, I, P or V, X16 =
      T or I, X17 = R, W, L, K, V, T or I, X19 = A, L or
      I, X23 = A or G, X24 = T or E
<221> NAME/KEY: VARIANT
<222> LOCATION: 25, 28, 29, 31, 35, 36
<223> OTHER INFORMATION: X25 = A, V or F, X28 = V, I or Y, X29 = F, L,
      W, I or A, X31 = L or Q, X35 = A or D, X36 = K or N
<221> NAME/KEY: VARIANT
<222> LOCATION: 37, 38, 39, 41, 42, 45, 47, 48
<223> OTHER INFORMATION: X37 = T or G, X38 = V or I, X39 = E or D,
      X41 = V or E, X42 = W or F, X45 = D or K, X47 = E or A,
      X48 = T or I
<221> NAME/KEY: VARIANT
<222> LOCATION: 2
<223> OTHER INFORMATION: Xaa = aromatic hydrophobic
<221> NAME/KEY: VARIANT
<222> LOCATION: 4, 5, 6, 32, 51, 53
<223> OTHER INFORMATION: Xaa = hydrophobic
<221> NAME/KEY: VARIANT
<222> LOCATION: 33
<223> OTHER INFORMATION: Xaa = non aromatic hydrophobic

<400> SEQUENCE: 43

```
Thr Xaa Lys Xaa Xaa Xaa Xaa Xaa Xaa Xaa Xaa Xaa Xaa Xaa Xaa
 1               5                   10                  15

Xaa Glu Xaa Val Asp Ala Xaa Xaa Xaa Glu Lys Xaa Xaa Lys Xaa Xaa
                 20                  25                  30

Xaa Asn Xaa Xaa Xaa Xaa Xaa Gly Xaa Xaa Thr Tyr Xaa Asp Xaa Xaa
             35                  40                  45

Lys Thr Xaa Thr Xaa Thr Glu
     50              55

<210> SEQ ID NO 44
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 5, 6, 7, 8, 9
<223> OTHER INFORMATION: X2 = Y,F,W or A, X4 = L,V,I,M,F,Y or A, X5 =
      L,V,I,F or M, X6 = L, V, I, F, M, A, Y or S,
      X7 = N or V, X8 = G, L or I, X9 = K or G
<221> NAME/KEY: VARIANT
<222> LOCATION: 10, 11, 12, 13, 14, 15, 16
<223> OTHER INFORMATION: X10 = Q, T or D, X11 = L, A or R, X12 = K or V,
      X13 = G, E or V , X14 = E or V, X15 = A, T, R, I,
      P or V, X16 = T or I
<221> NAME/KEY: VARIANT
<222> LOCATION: 17, 19, 23, 24
<223> OTHER INFORMATION: X17 = R, W, L, K, V, T or I, X19 = A, L or I,
      X23 = A or G, X24 = T or E
<221> NAME/KEY: VARIANT
<222> LOCATION: 25, 28, 29, 31, 32, 33, 35, 36
<223> OTHER INFORMATION: X25 = A, V or F, X28 = V, I or Y, X29 = F, L,
      W, I or A, X31 = L or Q, X32 = W, F, L, M, Y or I, X33 = L, V,
      I or A, X35 = A or D, X36 = K or N
<221> NAME/KEY: VARIANT
<222> LOCATION: 37, 38, 39, 41, 42, 45, 47, 48, 51, 53
<223> OTHER INFORMATION: X37 = T or G, X38 = V or I, X39 = E or D,
      X41 = V or E, X42 = W or F, X45 = D or K, X47 = E or A, X48 = T or
      I , X51 = L, V, I, F, M or W, X53 = L, V, I, F or M

<400> SEQUENCE: 44

Thr Xaa Lys Xaa Xaa Xaa Xaa Xaa Xaa Xaa Xaa Xaa Xaa Xaa Xaa
 1               5                   10                  15

Xaa Glu Xaa Val Asp Ala Xaa Xaa Xaa Glu Lys Xaa Xaa Lys Xaa Xaa
                 20                  25                  30

Xaa Asn Xaa Xaa Xaa Xaa Xaa Gly Xaa Xaa Thr Tyr Xaa Asp Xaa Xaa
             35                  40                  45

Lys Thr Xaa Thr Xaa Thr Glu
     50              55

<210> SEQ ID NO 45
<211> LENGTH: 201
<212> TYPE: DNA
<213> ORGANISM: Artificial Sequence
<220> FEATURE:
<223> OTHER INFORMATION: Synthetic polynucleotide

<400> SEQUENCE: 45
gatgataaag gcggtagcac gtacaaactg attctgaacg gcaaaaccct gaaaggtgaa       60
accacgaccg aagcagtgga tgcagcaacg gcagaaaaag tttttcaaaca gtacgccaac     120 gataatggcg tggatggtga atggacctac gatgatgcga cgaaaaacctt cacggttacc    180 gaaggcggtt ctgacaaaac t                                                201

<210> SEQ ID NO 46
```

```
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 46

Asp Asp Lys Gly Gly Ser Thr Tyr Lys Leu Ile Leu Asn Gly Lys Thr
 1               5                  10                  15

Leu Lys Gly Glu Thr Thr Thr Glu Ala Val Asp Ala Ala Thr Ala Glu
            20                  25                  30

Lys Val Phe Lys Gln Tyr Ala Asn Asp Asn Gly Val Asp Gly Glu Trp
        35                  40                  45

Thr Tyr Asp Asp Ala Thr Lys Thr Phe Thr Val Thr Glu Gly Gly Ser
50                  55                  60

Asp Lys Thr
65

<210> SEQ ID NO 47
<211> LENGTH: 55
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 21, 22, 23, 24, 26, 27, 30, 31, 34, 35, 37, 38, 39, 40,
      41
<223> OTHER INFORMATION: Xaa = Any Amino Acid

<400> SEQUENCE: 47

Thr Tyr Lys Leu Ile Leu Asn Gly Lys Thr Leu Lys Gly Glu Thr Thr
 1               5                  10                  15

Thr Glu Ala Val Xaa Xaa Xaa Xaa Ala Xaa Xaa Val Phe Xaa Xaa Tyr
            20                  25                  30

Ala Xaa Xaa Asn Xaa Xaa Xaa Xaa Xaa Trp Thr Tyr Asp Asp Ala Thr
        35                  40                  45

Lys Thr Phe Thr Val Thr Glu
50                  55

<210> SEQ ID NO 48
<211> LENGTH: 55
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 18, 19, 20, 21, 22, 23, 24, 26, 27, 28, 30, 31, 32, 34,
      35
<223> OTHER INFORMATION: Xaa = Any Amino Acid

<400> SEQUENCE: 48

Thr Tyr Lys Leu Ile Leu Asn Gly Lys Thr Leu Lys Gly Glu Thr Thr
 1               5                  10                  15

Thr Xaa Xaa Xaa Xaa Xaa Xaa Xaa Ala Xaa Xaa Xaa Phe Xaa Xaa Xaa
            20                  25                  30

Ala Xaa Xaa Asn Gly Val Asp Gly Glu Trp Thr Tyr Asp Asp Ala Thr
        35                  40                  45

Lys Thr Phe Thr Val Thr Glu
50                  55

<210> SEQ ID NO 49
```

-continued

```
<211> LENGTH: 55
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1, 18, 19, 20, 21, 22, 23, 24, 45, 46, 47, 48, 49
<223> OTHER INFORMATION: Xaa = Any Amino Acid

<400> SEQUENCE: 49

Xaa Tyr Lys Leu Ile Leu Asn Gly Lys Thr Leu Lys Gly Glu Thr Thr
 1               5                  10                  15

Thr Xaa Xaa Xaa Xaa Xaa Xaa Xaa Ala Glu Lys Val Phe Lys Gln Tyr
            20                  25                  30

Ala Asn Asp Asn Gly Val Asp Gly Glu Trp Thr Tyr Xaa Xaa Xaa Xaa
        35                  40                  45

Xaa Thr Phe Thr Val Thr Glu
        50                  55

<210> SEQ ID NO 50
<211> LENGTH: 55
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7, 8, 9, 10, 11, 12, 36, 37, 38, 39, 40, 41, 54, 55
<223> OTHER INFORMATION: Xaa = Any Amino Acid

<400> SEQUENCE: 50

Thr Tyr Lys Leu Ile Leu Xaa Xaa Xaa Xaa Xaa Xaa Gly Glu Thr Thr
 1               5                  10                  15

Thr Glu Ala Val Asp Ala Ala Thr Ala Glu Lys Val Phe Lys Gln Tyr
            20                  25                  30

Ala Asn Asp Xaa Xaa Xaa Xaa Xaa Xaa Trp Thr Tyr Asp Asp Ala Thr
        35                  40                  45

Lys Thr Phe Thr Val Xaa Xaa
        50                  55

<210> SEQ ID NO 51
<211> LENGTH: 55
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3, 5, 7, 8, 9, 10, 11, 12, 13, 14, 16, 52, 54, 55
<223> OTHER INFORMATION: Xaa = Any Amino Acid

<400> SEQUENCE: 51

Thr Tyr Xaa Leu Xaa Leu Xaa Xaa Xaa Xaa Xaa Xaa Xaa Xaa Thr Xaa
 1               5                  10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Xaa Val Xaa Xaa
        50                  55

<210> SEQ ID NO 52
<211> LENGTH: 55
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1, 3, 5, 7, 41, 43, 45, 46, 47, 48, 49, 50, 52, 54
<223> OTHER INFORMATION: Xaa = Any Amino Acid

<400> SEQUENCE: 52

Xaa Tyr Xaa Leu Xaa Leu Xaa Gly Lys Thr Leu Lys Gly Glu Thr Thr
 1               5                  10                  15

Thr Glu Ala Val Asp Ala Ala Thr Ala Glu Lys Val Phe Lys Gln Tyr
            20                  25                  30

Ala Asn Asp Asn Gly Val Asp Gly Xaa Trp Xaa Tyr Xaa Xaa Xaa Xaa
        35                  40                  45

Xaa Xaa Phe Xaa Val Xaa Glu
    50                  55
```